(12) United States Patent
Waldhauser et al.

(10) Patent No.: US 10,894,160 B2
(45) Date of Patent: Jan. 19, 2021

(54) CATHETER AND ELECTRODE SYSTEMS FOR ELECTRICAL NEUROMODULATION

(71) Applicant: Cardionomic, Inc., New Brighton, MN (US)

(72) Inventors: Steven L. Waldhauser, Savage, MN (US); Steven D. Goedeke, Forest Lake, MN (US); Duane G. Frion, Brooklyn Center, MN (US)

(73) Assignee: Cardionomic, Inc., New Brighton, MN (US)

( * ) Notice: Subject to any disclaimer, the term of this patent is extended or adjusted under 35 U.S.C. 154(b) by 427 days.

(21) Appl. No.: 15/446,872

(22) Filed: Mar. 1, 2017

(65) Prior Publication Data

US 2017/0173338 A1 Jun. 22, 2017

Related U.S. Application Data

(63) Continuation of application No. PCT/US2015/047770, filed on Aug. 31, 2015.
(Continued)

(51) Int. Cl.
*A61N 1/00* (2006.01)
*A61N 1/36* (2006.01)
(Continued)

(52) U.S. Cl.
CPC ....... *A61N 1/36114* (2013.01); *A61M 25/005* (2013.01); *A61M 25/007* (2013.01);
(Continued)

(58) Field of Classification Search
CPC .. A61N 1/0551; A61N 1/0553; A61N 1/0556; A61N 1/0558; A61N 1/517; A61N 1/519; A61N 1/056; A61N 1/057
See application file for complete search history.

(56) References Cited

U.S. PATENT DOCUMENTS

| 4,718,423 A | 1/1988 | Willis et al. |
| 4,947,866 A | 8/1990 | Lessar et al. |

(Continued)

FOREIGN PATENT DOCUMENTS

| CA | 2 848 781 | 3/2013 |
| EP | 1 871 469 | 10/2013 |

(Continued)

OTHER PUBLICATIONS

Ardell et al., "Differential sympathetic regulation of automatic, conductile, and contractile tissue in dog heart," American Journal of Physiology (Nov. 1988) 255 (5): H1050-H1059.
(Continued)

*Primary Examiner* — Scott M. Getzow
(74) *Attorney, Agent, or Firm* — Knobbe Martens Olson & Bear, LLP

(57) ABSTRACT

Embodiments of the present disclosure provide for catheters for use in electrical neuromodulation. The catheter of the present disclosure includes an elongate body having a first end and a second end. The elongate body includes a longitudinal center axis that extends between the first end and the second end. The elongate body further includes three or more surfaces that define a convex polygonal cross-sectional shape taken perpendicularly to the longitudinal center axis. The catheter further includes one or more electrodes on one surface of the three or more surfaces of the elongate body, where conductive elements extend through the elongate body. The conductive elements can conduct electrical current to combinations of the one or more electrodes.

20 Claims, 12 Drawing Sheets

Related U.S. Application Data

(60) Provisional application No. 62/047,270, filed on Sep. 8, 2014.

(51) Int. Cl.
*A61M 25/01* (2006.01)
*A61N 1/05* (2006.01)
*A61M 25/00* (2006.01)
*A61M 25/09* (2006.01)
*A61M 25/10* (2013.01)

(52) U.S. Cl.
CPC ........ *A61M 25/0147* (2013.01); *A61M 25/09* (2013.01); *A61M 25/10* (2013.01); *A61N 1/0558* (2013.01); *A61N 1/0587* (2013.01); *A61N 1/36132* (2013.01); *A61M 2025/018* (2013.01)

(56) References Cited

U.S. PATENT DOCUMENTS

| | | |
|---|---|---|
| 4,950,227 A | 8/1990 | Savin et al. |
| 5,067,957 A | 11/1991 | Jervis |
| 5,156,154 A | 10/1992 | Valenta, Jr. et al. |
| 5,190,546 A | 3/1993 | Jervis |
| 5,197,978 A | 3/1993 | Hess |
| 5,213,098 A | 5/1993 | Bennett et al. |
| 5,224,491 A | 7/1993 | Mehra |
| 5,259,387 A | 11/1993 | Depinto |
| 5,336,244 A | 8/1994 | Weijand |
| 5,345,936 A | 9/1994 | Pomeranz et al. |
| 5,365,926 A | 11/1994 | Desai |
| 5,423,881 A | 6/1995 | Breyen et al. |
| 5,431,649 A | 7/1995 | Mulier et al. |
| 5,554,139 A | 9/1996 | Okajima |
| 5,564,434 A | 10/1996 | Halperin et al. |
| 5,598,848 A | 2/1997 | Swanson et al. |
| 5,711,316 A | 1/1998 | Elsberry et al. |
| 5,725,570 A | 3/1998 | Heath |
| 5,755,766 A | 5/1998 | Chastain et al. |
| 5,782,239 A * | 7/1998 | Webster, Jr. ......... A61B 5/0422 600/374 |
| 5,853,411 A | 12/1998 | Whayne et al. |
| 5,948,007 A | 9/1999 | Starkebaum et al. |
| 5,954,761 A | 9/1999 | Machek et al. |
| 5,968,040 A | 10/1999 | Swanson et al. |
| 5,997,563 A | 12/1999 | Kretzers |
| 6,036,697 A | 3/2000 | Dicaprio |
| 6,038,480 A | 3/2000 | Hrdlicka et al. |
| 6,058,331 A | 5/2000 | King et al. |
| 6,059,810 A | 5/2000 | Brown et al. |
| 6,071,308 A | 6/2000 | Ballou et al. |
| 6,136,021 A | 10/2000 | Tockman et al. |
| 6,152,882 A | 11/2000 | Prutchi |
| 6,161,029 A | 12/2000 | Spreigl et al. |
| 6,223,072 B1 | 4/2001 | Mika et al. |
| 6,231,516 B1 | 5/2001 | Keilman et al. |
| 6,233,484 B1 | 5/2001 | Ben-haim et al. |
| 6,233,487 B1 | 5/2001 | Mika et al. |
| 6,236,887 B1 | 5/2001 | Ben-haim et al. |
| 6,241,724 B1 | 6/2001 | Fleischman et al. |
| 6,254,610 B1 | 7/2001 | Darvish et al. |
| 6,263,242 B1 | 7/2001 | Mika et al. |
| 6,266,564 B1 | 7/2001 | Hill et al. |
| 6,285,906 B1 | 9/2001 | Ben-haim et al. |
| 6,292,693 B1 | 9/2001 | Darvish et al. |
| 6,292,695 B1 | 9/2001 | Webster et al. |
| 6,292,704 B1 | 9/2001 | Malonek et al. |
| 6,295,475 B1 | 9/2001 | Morgan |
| 6,298,268 B1 | 10/2001 | Ben-haim et al. |
| 6,304,777 B1 | 10/2001 | Ben-haim et al. |
| 6,317,631 B1 | 11/2001 | Ben-haim et al. |
| 6,319,241 B1 | 11/2001 | King et al. |
| 6,330,476 B1 | 12/2001 | Ben-haim et al. |
| 6,335,538 B1 | 1/2002 | Prutchi et al. |
| 6,348,045 B1 | 2/2002 | Malonek et al. |
| 6,353,762 B1 | 3/2002 | Baudino et al. |
| 6,360,123 B1 | 3/2002 | Kimchi et al. |
| 6,360,126 B1 | 3/2002 | Mika et al. |
| 6,363,279 B1 | 3/2002 | Ben-haim et al. |
| 6,370,430 B1 | 4/2002 | Mika et al. |
| 6,415,178 B1 | 7/2002 | Ben-haim et al. |
| 6,424,866 B2 | 7/2002 | Mika et al. |
| 6,428,537 B1 | 8/2002 | Swanson et al. |
| 6,442,424 B1 | 8/2002 | Ben-haim et al. |
| 6,447,478 B1 | 9/2002 | Maynard |
| 6,459,928 B2 | 10/2002 | Mika et al. |
| 6,463,324 B1 | 10/2002 | Ben-haim et al. |
| 6,473,653 B1 | 10/2002 | Schallhorn et al. |
| 6,480,737 B1 | 11/2002 | Policker et al. |
| 6,522,904 B1 | 2/2003 | Mika et al. |
| 6,522,926 B1 | 2/2003 | Kieval et al. |
| 6,529,778 B2 | 3/2003 | Prutchi |
| 6,542,774 B2 | 4/2003 | Hill et al. |
| 6,547,788 B1 | 4/2003 | Maguire et al. |
| 6,564,096 B2 | 5/2003 | Mest |
| 6,571,127 B1 | 5/2003 | Ben-haim et al. |
| 6,574,492 B1 | 6/2003 | Shlomo et al. |
| 6,587,721 B1 | 7/2003 | Prutchi et al. |
| 6,597,952 B1 | 7/2003 | Mika et al. |
| 6,600,953 B2 | 7/2003 | Flesler et al. |
| 6,662,055 B1 | 12/2003 | Prutchi |
| 6,669,693 B2 | 12/2003 | Friedman |
| 6,675,043 B1 | 1/2004 | Prutchi et al. |
| 6,684,105 B2 | 1/2004 | Cohen et al. |
| 6,694,192 B2 | 2/2004 | Policker et al. |
| 6,712,831 B1 | 3/2004 | Kaplan et al. |
| 6,725,093 B1 | 4/2004 | Ben-haim et al. |
| 6,738,655 B1 | 5/2004 | Sen et al. |
| 6,740,113 B2 | 5/2004 | Vrba |
| 6,748,271 B2 | 6/2004 | Spinelli et al. |
| 6,749,600 B1 | 6/2004 | Levy |
| 6,754,532 B1 | 6/2004 | Ferek-Petric |
| RE38,654 E | 11/2004 | Hill et al. |
| 6,832,478 B2 | 12/2004 | Anderson et al. |
| 6,850,801 B2 | 2/2005 | Kieval et al. |
| 6,887,266 B2 | 5/2005 | Williams et al. |
| 6,912,419 B2 | 6/2005 | Hill et al. |
| 6,932,930 B2 | 8/2005 | Desimone et al. |
| 6,944,490 B1 | 9/2005 | Chow |
| 6,947,792 B2 | 9/2005 | Ben-haim et al. |
| 6,950,689 B1 | 9/2005 | Willis et al. |
| 6,985,774 B2 | 1/2006 | Kieval et al. |
| 6,993,385 B1 | 1/2006 | Routh et al. |
| 7,027,863 B1 | 4/2006 | Prutchi et al. |
| 7,062,318 B2 | 6/2006 | Ben-haim et al. |
| 7,072,720 B2 | 7/2006 | Puskas |
| 7,082,336 B2 | 7/2006 | Ransbury et al. |
| 7,092,753 B2 | 8/2006 | Darvish et al. |
| 7,092,759 B2 | 8/2006 | Nehls et al. |
| 7,096,070 B1 | 8/2006 | Jenkins et al. |
| 7,097,665 B2 | 8/2006 | Stack et al. |
| 7,111,627 B2 | 9/2006 | Stack et al. |
| 7,121,283 B2 | 10/2006 | Stack et al. |
| 7,141,061 B2 | 11/2006 | Williams et al. |
| 7,146,984 B2 | 12/2006 | Stack et al. |
| 7,152,607 B2 | 12/2006 | Stack et al. |
| 7,158,832 B2 | 1/2007 | Kieval et al. |
| 7,163,554 B2 | 1/2007 | Williams et al. |
| 7,167,748 B2 | 1/2007 | Ben-haim et al. |
| 7,171,263 B2 | 1/2007 | Darvish et al. |
| 7,187,970 B2 | 3/2007 | Shemer et al. |
| 7,190,997 B1 | 3/2007 | Darvish et al. |
| 7,195,594 B2 | 3/2007 | Eigler et al. |
| 7,195,637 B2 | 3/2007 | Mika |
| 7,218,963 B2 | 5/2007 | Ben-haim et al. |
| 7,231,260 B2 | 6/2007 | Wallace et al. |
| 7,260,431 B2 | 8/2007 | Libbus et al. |
| 7,277,757 B2 | 10/2007 | Casavant et al. |
| 7,277,761 B2 | 10/2007 | Shelchuk |
| 7,279,007 B2 | 10/2007 | Nikolic |
| 7,285,287 B2 | 10/2007 | Williams et al. |
| 7,295,881 B2 | 11/2007 | Cohen et al. |
| 7,308,303 B2 | 12/2007 | Whitehurst et al. |

(56) References Cited

U.S. PATENT DOCUMENTS

| | | |
|---|---|---|
| 7,310,555 B2 | 12/2007 | Ben-haim et al. |
| 7,321,793 B2 | 1/2008 | Ben Ezra et al. |
| 7,354,454 B2 | 4/2008 | Stack et al. |
| 7,363,082 B2 | 4/2008 | Ransbury et al. |
| 7,377,939 B2 | 5/2008 | Williams et al. |
| 7,389,149 B2 | 6/2008 | Rossing et al. |
| 7,412,289 B2 | 8/2008 | Malonek et al. |
| 7,431,725 B2 | 10/2008 | Stack et al. |
| 7,460,906 B2 | 12/2008 | Libbus |
| 7,460,907 B1 | 12/2008 | Darvish et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,529,589 B2 | 5/2009 | Williams et al. |
| 7,542,800 B2 | 6/2009 | Libbus et al. |
| 7,547,286 B2 | 6/2009 | Choate |
| 7,561,923 B2 | 7/2009 | Libbus et al. |
| 7,616,997 B2 | 11/2009 | Kieval et al. |
| 7,617,003 B2 | 11/2009 | Caparso et al. |
| 7,617,007 B2 | 11/2009 | Williams et al. |
| 7,623,926 B2 | 11/2009 | Rossing et al. |
| 7,630,760 B2 | 12/2009 | Libbus et al. |
| 7,634,317 B2 | 12/2009 | Ben-David et al. |
| 7,643,875 B2 | 1/2010 | Heil, Jr. et al. |
| 7,647,102 B2 | 1/2010 | Routh et al. |
| 7,658,709 B2 | 2/2010 | Anderson et al. |
| 7,668,602 B2 | 2/2010 | Ben-David et al. |
| 7,676,266 B1 | 3/2010 | Kroll |
| 7,704,276 B2 | 4/2010 | Williams et al. |
| 7,706,884 B2 | 4/2010 | Libbus |
| 7,734,343 B2 | 6/2010 | Ransbury et al. |
| 7,734,348 B2 | 6/2010 | Zhang et al. |
| 7,747,335 B2 | 6/2010 | Williams |
| 7,765,000 B2 | 7/2010 | Zhang et al. |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,801,614 B2 | 9/2010 | Rossing et al. |
| 7,805,194 B1 | 9/2010 | Schecter |
| 7,805,203 B2 | 9/2010 | Ben-David et al. |
| 7,813,812 B2 | 10/2010 | Kieval et al. |
| 7,840,262 B2 | 11/2010 | Mika et al. |
| 7,840,271 B2 | 11/2010 | Kieval et al. |
| 7,840,282 B2 | 11/2010 | Williams et al. |
| 7,848,812 B2 | 12/2010 | Crowley et al. |
| 7,857,748 B2 | 12/2010 | Williams et al. |
| 7,869,881 B2 | 1/2011 | Libbus et al. |
| 7,873,413 B2 | 1/2011 | McCabe et al. |
| 7,881,782 B2 | 2/2011 | Libbus et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,892,292 B2 | 2/2011 | Stack et al. |
| 7,899,554 B2 | 3/2011 | Williams et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,919,162 B2 | 4/2011 | Desimone et al. |
| 7,925,352 B2 | 4/2011 | Stack et al. |
| 7,949,400 B2 | 5/2011 | Kieval et al. |
| 7,953,481 B1 | 5/2011 | Shemer et al. |
| 7,966,067 B2 | 6/2011 | Rousso et al. |
| 7,974,693 B2 | 7/2011 | Ben-David et al. |
| 8,000,793 B2 | 8/2011 | Libbus |
| 8,005,542 B2 | 8/2011 | Ben-Ezra et al. |
| 8,005,545 B2 | 8/2011 | Ben-David et al. |
| 8,014,858 B1 | 9/2011 | Ben-haim et al. |
| 8,014,874 B2 | 9/2011 | Rossing et al. |
| 8,024,050 B2 | 9/2011 | Libbus et al. |
| 8,027,724 B2 | 9/2011 | Wei et al. |
| 8,032,215 B2 | 10/2011 | Libbus et al. |
| 8,036,745 B2 | 10/2011 | Ben-David et al. |
| 8,060,197 B2 | 11/2011 | Ben-David et al. |
| 8,060,206 B2 | 11/2011 | Kieval et al. |
| 8,060,218 B2 | 11/2011 | Singh et al. |
| 8,086,314 B1 | 12/2011 | Kieval |
| 8,116,881 B2 | 2/2012 | Cohen et al. |
| 8,116,883 B2 | 2/2012 | Williams et al. |
| 8,121,693 B2 | 2/2012 | Libbus |
| 8,126,560 B2 | 2/2012 | Schiener et al. |
| 8,131,373 B2 | 3/2012 | Libbus |
| 8,145,304 B2 | 3/2012 | Moffitt et al. |
| 8,150,521 B2 | 4/2012 | Crowley et al. |
| 8,152,843 B2 | 4/2012 | Williams et al. |
| 8,155,744 B2 | 4/2012 | Rezai |
| 8,175,705 B2 | 5/2012 | Libbus |
| 8,195,289 B2 | 6/2012 | Heil, Jr. et al. |
| 8,195,290 B2 | 6/2012 | Brockway et al. |
| 8,204,591 B2 | 6/2012 | Ben-David et al. |
| 8,204,596 B2 | 6/2012 | Ransbury et al. |
| 8,206,456 B2 | 6/2012 | Stack et al. |
| 8,224,444 B2 | 7/2012 | Ben-David et al. |
| 8,229,564 B2 | 7/2012 | Rezai |
| 8,239,037 B2 | 8/2012 | Glenn et al. |
| 8,239,045 B2 | 8/2012 | Ransbury et al. |
| 8,244,355 B2 | 8/2012 | Bennett et al. |
| 8,249,706 B2 | 8/2012 | Koh |
| 8,260,416 B2 | 9/2012 | Ben-haim et al. |
| 8,290,595 B2 | 10/2012 | Kieval et al. |
| 8,301,247 B2 | 10/2012 | Ben-haim et al. |
| 8,306,616 B2 | 11/2012 | Ben-haim et al. |
| 8,306,617 B2 | 11/2012 | Ben-haim et al. |
| 8,311,629 B2 | 11/2012 | Ben-haim et al. |
| 8,311,633 B2 | 11/2012 | Ransbury et al. |
| 8,321,013 B2 | 11/2012 | Darvish et al. |
| 8,326,416 B2 | 12/2012 | Mika et al. |
| 8,335,571 B2 | 12/2012 | Singh et al. |
| 8,352,031 B2 | 1/2013 | Rousso et al. |
| 8,369,954 B2 | 2/2013 | Stack et al. |
| 8,372,325 B2 | 2/2013 | Williams et al. |
| 8,386,053 B2 | 2/2013 | Kornet |
| 8,386,056 B2 | 2/2013 | Ben-David et al. |
| 8,401,672 B2 | 3/2013 | Libbus et al. |
| 8,406,864 B2 | 3/2013 | Rousso et al. |
| 8,406,877 B2 | 3/2013 | Smith et al. |
| 8,412,326 B2 | 4/2013 | Arcot-Krishnamurthy et al. |
| 8,417,354 B2 | 4/2013 | Zhang et al. |
| 8,428,730 B2 | 4/2013 | Stack et al. |
| 8,437,867 B2 | 5/2013 | Murney et al. |
| 8,452,398 B2 | 5/2013 | Libbus et al. |
| 8,473,076 B2 | 6/2013 | Libbus et al. |
| 8,498,703 B2 | 7/2013 | Spinelli et al. |
| 8,538,535 B2 | 9/2013 | Gross et al. |
| 8,548,583 B2 | 10/2013 | Rousso et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,583,236 B2 | 11/2013 | Kieval et al. |
| 8,606,359 B2 | 12/2013 | Rossing et al. |
| 8,609,082 B2 | 12/2013 | Ben-David et al. |
| 8,615,294 B2 | 12/2013 | Ben-David et al. |
| 8,620,426 B2 | 12/2013 | Moffitt et al. |
| 8,626,290 B2 | 1/2014 | Dagan et al. |
| 8,626,299 B2 | 1/2014 | Gross et al. |
| 8,634,921 B2 | 1/2014 | Chavan et al. |
| 8,639,332 B2 | 1/2014 | Kuhn et al. |
| 8,655,444 B2 | 2/2014 | Ben-haim et al. |
| 8,682,430 B2 | 3/2014 | Libbus et al. |
| 8,682,434 B2 | 3/2014 | Libbus |
| 8,706,230 B2 | 4/2014 | Rousso et al. |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,771,337 B2 | 7/2014 | Williams et al. |
| 8,784,354 B2 | 7/2014 | Stack et al. |
| 8,784,500 B2 | 7/2014 | Stack et al. |
| 8,788,066 B2 | 7/2014 | Cates et al. |
| 8,798,738 B2 | 8/2014 | Machado et al. |
| 8,805,501 B2 | 8/2014 | Libbus |
| 8,818,501 B2 | 8/2014 | Machado et al. |
| 8,825,152 B2 | 9/2014 | Shemer et al. |
| 8,838,246 B2 | 9/2014 | Kieval |

(56) References Cited

U.S. PATENT DOCUMENTS

| | | |
|---|---|---|
| 8,855,783 B2 | 10/2014 | Dagan et al. |
| 8,880,190 B2 | 11/2014 | Kieval et al. |
| 8,886,340 B2 | 11/2014 | Williams et al. |
| 8,901,878 B2 | 12/2014 | Prutchi et al. |
| 8,906,286 B2 | 12/2014 | Desimone et al. |
| 8,918,172 B2 | 12/2014 | Moffitt et al. |
| 8,929,990 B2 | 1/2015 | Moffitt et al. |
| 8,934,956 B2 | 1/2015 | Glenn et al. |
| 8,934,968 B2 | 1/2015 | Whitehurst et al. |
| 8,958,872 B2 | 2/2015 | Ben-haim et al. |
| 8,972,015 B2 | 3/2015 | Stack et al. |
| 8,977,353 B2 | 3/2015 | Rousso et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-haim et al. |
| 9,216,289 B2 | 12/2015 | Libbus et al. |
| 9,248,038 B2 | 2/2016 | Stack et al. |
| 9,289,618 B1 | 3/2016 | Ben-haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 2003/0045909 A1 | 3/2003 | Gross et al. |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0100668 A1 | 5/2006 | Ben-David et al. |
| 2006/0116737 A1 | 6/2006 | Libbus |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0135875 A1* | 6/2007 | Demarais ............ A61F 7/123 607/96 |
| 2007/0255364 A1* | 11/2007 | Gerber ............ A61N 1/0534 607/116 |
| 2008/0015659 A1 | 1/2008 | Zhang et al. |
| 2008/0046016 A1 | 2/2008 | Ben-David et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0161894 A1 | 7/2008 | Ben-David et al. |
| 2008/0167693 A1 | 7/2008 | Kieval et al. |
| 2008/0177338 A1 | 7/2008 | Ben-David et al. |
| 2008/0275349 A1 | 11/2008 | Halperin et al. |
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0276022 A1 | 11/2009 | Burnes et al. |
| 2009/0281608 A1* | 11/2009 | Foster ............ A61B 5/0422 607/127 |
| 2010/0222832 A1 | 9/2010 | Zhang et al. |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1* | 2/2012 | Haverkost ......... A61B 18/1492 606/41 |
| 2012/0232563 A1 | 9/2012 | Williams et al. |
| 2012/0303080 A1 | 11/2012 | Ben-David et al. |
| 2012/0310304 A1 | 12/2012 | Brockway et al. |
| 2013/0012863 A1 | 1/2013 | Stack et al. |
| 2013/0110208 A1 | 5/2013 | Inagaki et al. |
| 2013/0172715 A1 | 7/2013 | Just et al. |
| 2013/0218221 A1 | 8/2013 | Zhang et al. |
| 2013/0253616 A1 | 9/2013 | Libbus et al. |
| 2013/0289686 A1 | 10/2013 | Masson et al. |
| 2013/0331919 A1 | 12/2013 | Zhang et al. |
| 2013/0338748 A1 | 12/2013 | Dagan |
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0172006 A1 | 6/2014 | Stack et al. |
| 2014/0214135 A1 | 7/2014 | Ben-David et al. |

(56) References Cited

U.S. PATENT DOCUMENTS

| | | |
|---|---|---|
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0324115 A1 | 10/2014 | Ziegler et al. |
| 2015/0018908 A1 | 1/2015 | Williams et al. |
| 2015/0039058 A1 | 2/2015 | Masson et al. |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2016/0022890 A1 | 1/2016 | Schwammenthal et al. |
| 2016/0051741 A1 | 2/2016 | Schwammenthal et al. |
| 2016/0174864 A1 | 6/2016 | Levin et al. |
| 2017/0001015 A1 | 1/2017 | Marnfeldt et al. |
| 2017/0036014 A1 | 2/2017 | Machado et al. |
| 2017/0065812 A1 | 3/2017 | Goedeke et al. |
| 2017/0065818 A1 | 3/2017 | Ransbury et al. |
| 2017/0143227 A1 | 5/2017 | Marecki et al. |
| 2017/0173339 A1 | 6/2017 | Waldhauser et al. |
| 2017/0189642 A1 | 7/2017 | Masson et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0050206 A1 | 2/2018 | Waldhauser et al. |
| 2018/0147408 A1 | 5/2018 | Machado et al. |

FOREIGN PATENT DOCUMENTS

| | | |
|---|---|---|
| EP | 2 316 525 | 1/2016 |
| WO | WO 1997/024983 | 7/1997 |
| WO | WO 2005/041748 | 5/2005 |
| WO | WO 2006/007048 | 1/2006 |
| WO | WO 2006/058253 | 6/2006 |
| WO | WO 2008/054448 | 5/2008 |
| WO | WO 2009/135083 | 11/2009 |
| WO | WO 2012/068273 | 5/2012 |
| WO | WO 2012/149511 | 11/2012 |
| WO | WO 2015/179634 | 11/2015 |
| WO | WO 2016/040038 | 3/2016 |
| WO | WO 2016/111940 | 7/2016 |
| WO | WO 2017/156039 | 9/2017 |

OTHER PUBLICATIONS

Casadei, "Vagal control of myocardial . . . in humans," The Physiological Society (Mar. 2001): 817-823.

De Ferrari et al., "Vagus nerve stimulation . . . future directions," Heart Fail Rev. (2011) 16: 195-203.

Klein et al., "Vagus nerve stimulation . . . heart failure," Cariology Journal (2010) 17 (6): 638-643.

Koizumi et al., "Functional significance of coactivation . . . ," National Academy of Sciences (Mar. 1982) 79 (6): 2116-2120.

Meyer et al., "Augmentation of left ventricular . . . ," Americ. Heart Assoc. (2010): 1286-1294.

Murphy, "Preliminary observations of the effects of simulation of . . . in man," CA Journal of Phys. and Pharmac (Jun. 1985). 63 (6): 649-655.

Randall et al., "Regional cardiac distribution . . . ," Federation Proceedings (Jul.-Aug. 1972) 31 (4): 1199-1208.

Randall, "Augmentor action to the sympathetic . . . ," Journal of Applied Physiology (Jul. 1960) 15 (4): 629-631.

Triposkiadis et al., "Sympathetic nervous . . . failure," Journal of Amer. Coll. of Cardiology (Nov. 3, 2009) 54 (19): 1747-1762.

Zarse, "Selective increase . . . sympathetic tone," Journal of Amer. Coll. of Cardiology (2005) 46 (7): 1354-1359.

Lawo et al., "Electrical Signals Applied During the Absolute Refractory Period", JACC, Dec. 20, 2005, vol. 46, No. 21, pp. 2229-2236.

Rudski et al., "Guidelines for the Echocardiographic Assessment of the Right Heart in Adults: A Report from the American Society of Echocardiography", J Am Soc Echocardiogr, 2010, vol. 23, pp. 685-713.

International Search Report and Written Opinion issued in PCT Application No. PCT/US2015/047770, dated Feb. 26, 2016, in 15 pages.

Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprlW.mjjo, downloaded on Oct. 30, 2017.

\* cited by examiner

CATHETER AND ELECTRODE SYSTEMS FOR ELECTRICAL NEUROMODULATION

TECHNICAL FIELD

The present disclosure relates generally to catheters, and more particularly to catheter and electrode systems for use in electrical neuromodulation.

BACKGROUND

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of the patient's congestive state.

Treatments for acute heart failure include the use of inotropic agents, such as dopamine and dobutamine. These agents, however, have both chronotropic and inotropic effects and characteristically increase heart contractility at the expense of significant increments in oxygen consumption secondary to elevations in heart rate. As a result, although these inotropic agents increase myocardial contractility and improve hemodynamics, clinical trials have consistently demonstrated excess mortality caused by cardiac arrhythmias and increase in the myocardium consumption.

As such, there is a need for selectively and locally treating acute heart failure and otherwise achieving hemodynamic control without causing unwanted systemic effects.

SUMMARY

Embodiments of the present disclosure provide for catheter and electrode systems for use in electrical neuromodulation. The catheter and electrode systems of the present disclosure, for example, may be useful in electrical neuromodulation of patients with cardiac disease, such as patients with chronic cardiac disease. As discussed herein, the configuration of the catheter and electrode systems of the present disclosure allows for a portion of the catheter to be positioned within the vasculature of the patient in the main pulmonary artery and/or one or both of the pulmonary arteries (the right pulmonary artery and/or the left pulmonary artery). Once positioned, the catheter and electrode systems of the present disclosure can provide electrical energy to stimulate the autonomic nerve fibers surrounding the main pulmonary artery and/or one or both of the pulmonary arteries in an effort to provide adjuvant cardiac therapy to the patient.

In a first example, the catheter of the present disclosure includes an elongate body having a first end and a second end. The elongate body includes a longitudinal center axis that extends between the first end and the second end. The elongate body further includes three or more surfaces that define a convex polygonal cross-sectional shape taken perpendicularly to the longitudinal center axis. The catheter further includes one or more, but preferably two or more, electrodes on one surface of the three or more surfaces of the elongate body, where conductive elements extend through the elongate body. The conductive elements can conduct electrical current to combinations of the one or more electrodes or in the instance of a single electrode a second electrode is provided elsewhere in the system for flow of current.

By way of example for the first embodiment, the surfaces defining the convex polygonal cross-sectional shape of the elongate body can be a rectangle. Other shapes are possible. In one embodiment, the one or two or more electrodes are only on the one surface of the three or more surfaces of the elongate body. The one or more electrodes can have an exposed face that is co-planar with the one surface of the three or more surfaces of the elongate body. The one surface of the three or more surfaces of the elongate body can further include anchor structures that extend above the one surface. In addition to the surfaces defining the convex polygonal cross-sectional shape, the elongate body of the catheter can also have a portion with a circular cross-section shape taken perpendicularly to the longitudinal center axis.

The catheter of the present embodiment can also include an inflatable balloon on a peripheral surface of the elongate body. The inflatable balloon includes a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon.

In a second example, the catheter of the present disclosure includes an elongate body having a peripheral surface and a longitudinal center axis extending between a first end and a second end. The elongate body of this second example has an offset region defined by a series of predefined curves along the longitudinal center axis. The predefined curves include a first portion having a first curve and a second curve in the longitudinal center axis, a second portion following the first portion, where the second portion has a zero curvature (e.g., a straight portion), and a third portion following the second portion, the third portion having a third curve and a fourth curve. An inflatable balloon is positioned on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. One or more electrodes are positioned on the elongate body along the second portion of the offset region of the elongate body. Conductive elements extend through the elongate body, where the conductive elements conduct electrical current to combinations of the one or more electrodes.

The portions of the elongate body of this second example can have a variety of shapes. For example, the second portion of the elongate body can form a portion of a helix. The elongate body can also have three or more surfaces defining a convex polygonal cross-sectional shape taken perpendicularly to the longitudinal center axis, where the one or more electrodes are on one surface of the three or more surfaces of the elongate body. For this embodiment, the convex polygonal cross-sectional shape can be a rectangle. The one or more electrodes are only on the one surface of the three or more surfaces of the elongate body. The one or more electrodes can have an exposed face that is co-planar with the one surface of the three or more surfaces of the elongate body.

In a third example, the catheter of the present disclosure includes an elongate body with a peripheral surface and a longitudinal center axis extending between a first end and a second end. The elongate body includes a surface defining a deflection lumen, where the deflection lumen includes a first opening and a second opening in the elongate body. An inflatable balloon is located on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. One or more electrodes are located on the elongate body, where the second opening of the deflection lumen is opposite the one or more electrodes on the elongate body. Conductive elements extend through the elongate body, where the conductive elements conduct electrical current to combinations of the one or more electrodes. The catheter also includes an elongate deflection member, where the elongate deflection member extends through the second opening of the deflection lumen in a direction opposite the one or more electrodes on one surface of the elongate body.

In a fourth example, the catheter of the present disclosure can include an elongate body having a peripheral surface and a longitudinal center axis extending between a first end and a second end. The elongate body includes a surface defining an electrode lumen, where the electrode lumen includes a first opening in the elongate body. The catheter further includes an inflatable balloon on the peripheral surface of the elongate body, the inflatable balloon having a balloon wall with an interior surface that along with a portion of the peripheral surface of the elongate body defines a fluid tight volume. An inflation lumen extends through the elongate body, the inflation lumen having a first opening into the fluid tight volume of the inflatable balloon and a second opening proximal to the first opening to allow for a fluid to move in the fluid tight volume to inflate and deflate the balloon. The catheter further includes an elongate electrode member, where the elongate electrode member extends through the first opening of the electrode lumen of the elongate body, where the electrode member includes one or more electrodes and conductive elements extending through the electrode lumen, where the conductive elements conduct electrical current to combinations of the one or more electrodes.

The elongate electrode member can form a loop that extends away from the peripheral surface of the elongate body. The elongate electrode member forming the loop can be in a plane that is co-linear with the longitudinal center axis of the elongate body. Alternatively, the elongate electrode member forming the loop is in a plane that is perpendicular to the longitudinal center axis of the elongate body.

DETAILED DESCRIPTION

Figure 1:
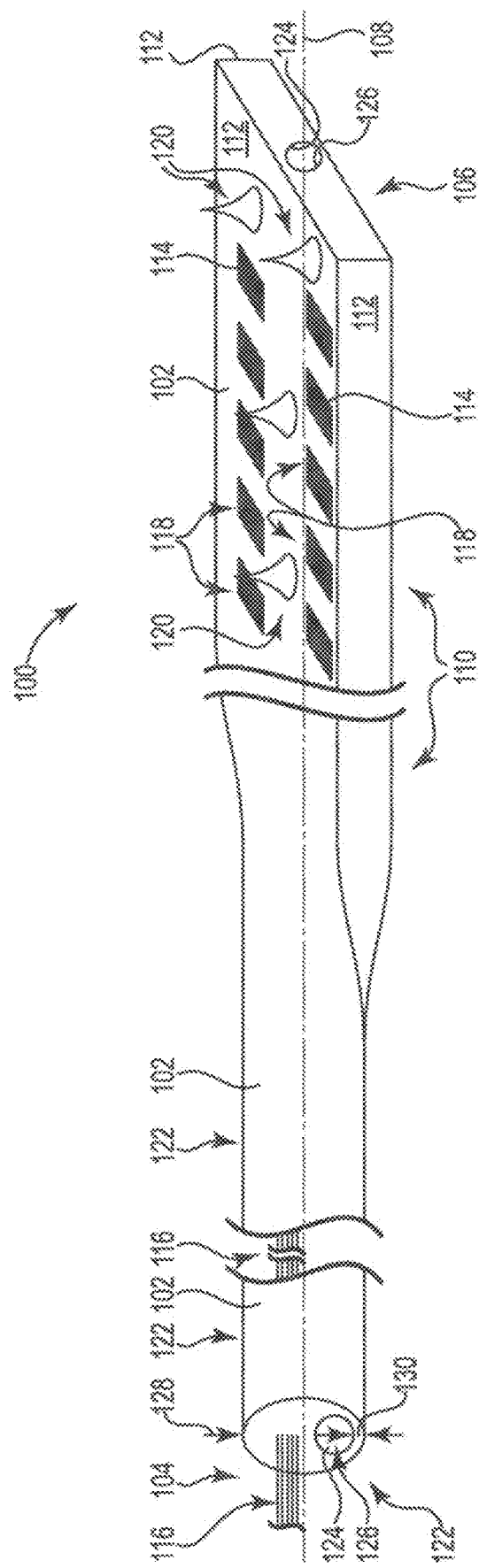
FIG. 1 provides an illustration of an embodiment of the catheter according to the present disclosure.

Embodiments of the present disclosure provide for a catheter and electrode systems for use in electrical neuromodulation. The catheter and electrode systems of the present disclosure, for example, may be useful in electrical neuromodulation of patients with cardiac disease, such as patients with chronic cardiac disease. As discussed herein, the configuration of the catheter and electrode systems of the present disclosure allows for a portion of the catheter and electrode systems to be positioned within the vasculature of the patient in the main pulmonary artery and at least one of the pulmonary arteries (the right pulmonary artery and/or the left pulmonary artery). Once positioned, the catheter and electrode systems of the present disclosure can be used to provide electrical energy to stimulate the autonomic nerve fibers surrounding the main pulmonary artery and/or one of the pulmonary arteries in an effort to provide adjuvant cardiac therapy to the patient.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or or eliminated so as to provide any number of additional embodiments of the present disclosure.

The terms "distal" and "proximal" are used in the following description with respect to a position or direction relative to the treating clinician taken along the catheter of the present disclosure. "Distal" or "distally" are a position distant from or in a direction away from the clinician. "Proximal" and "proximally" are a position near or in a direction toward the clinician taken along the catheter of the present disclosure.

The catheters and electrode systems provided herein includes one or more electrodes, but preferably two or more electrodes, as discussed herein. It is understood that the phrase one or more electrodes can be replaced herein with two or more electrodes if desired.

Referring to FIG. 1, there is shown a perspective view of a catheter 100 according one example of the present disclosure. The catheter 100 includes an elongate body 102 having a first end 104 and a second end 106 distal from the first end 104. As illustrated, the elongate body 102 includes a longitudinal center axis 108 extending between the first end 104 and the second end 106 of the elongate body 102. The elongate body 102 also includes a portion 110 that has three or more surfaces 112 defining a convex polygonal cross-sectional shape taken perpendicularly to the longitudinal center axis 108.

As used herein, the convex polygonal cross-sectional shape of the elongate body 102 includes those shapes for which every internal angle is less than 180 degrees and where every line segment between two vertices of the shape remains inside or on the boundary of the shape. Examples of such shapes include, but are not limited to, triangular, rectangular (as illustrated in FIG. 1), square, pentagon and hexagon, among others.

Catheter 100 further includes one or more, preferably two or more, electrodes 114 on one surface of the three or more surfaces 112 of the elongate body 102. Conductive elements 116 extend through the elongate body 102, where the conductive elements 116 can be used, as discussed herein, to conduct electrical current to combinations of the one or more electrodes 114. Each of the one or more electrodes 114 is coupled to a corresponding conductive element 116. The conductive elements 116 are electrically isolated from each other and extend through the elongate body 102 from each respective electrode 114 through the first end 104 of the elongate body 102. The conductive elements 116 terminate at a connector port, where each of the conductive elements 116 can be releasably coupled to a stimulation system, as discussed herein. It is also possible that the conductive elements 116 are permanently coupled to the stimulation system (e.g., not releasably coupled). The stimulation system can be used to provide stimulation electrical energy that is conducted through the conductive elements 116 and delivered across combinations of the one or more electrodes 114. The one or more electrodes 114 are electrically isolated from one another, where the elongate body 102 is formed of an electrically insulating material as discussed herein. As illustrated, the one or more electrodes 114 can be located only on the one surface of the three or more surfaces 112 of the elongate body 102.

There can be a variety of the number and the configuration of the one or more electrodes 114 on the one surface of the three or more surfaces 112 of the elongate body 102. For example, as illustrated, the one or more electrodes 114 can be configured as an array of electrodes, where the number of electrodes and their relative position to each other can vary depending upon the desired implant location. As discussed herein, the one or more electrodes 114 can be configured to allow for electrical current to be delivered from and/or between different combinations of the one or more electrodes 114. So, for example, the electrodes in the array of electrodes can have a repeating pattern where the electrodes are equally spaced from each other. For example, the electrodes in the array of electrodes can have a column and row configuration (as illustrated in FIG. 1). Alternatively, the electrodes in the array of electrodes can have a concentric radial pattern, where the electrodes are positioned so as to form concentric rings of the electrodes. Other patterns are possible, where such patterns can either be repeating patterns or random patterns.

As illustrated, the one or more electrodes 114 have an exposed face 118. The exposed face 118 of the electrode 114 provides the opportunity for the electrode 114, when implanted in the patient, to be placed into proximity and/or in contact with the vascular tissue of the patient, as opposed to facing into the volume of blood in the artery. As the one or more electrodes 114 are located on one surface of the three or more surfaces 112 of the elongate body 102, the electrodes 114 can be placed into direct proximity to and/or in contact with the tissue of any combination of the main pulmonary artery, the left pulmonary artery and/or the right pulmonary artery.

By locating the one or more electrodes 114 on the one surface of the three or more surfaces 112, the exposed face 118 of the electrode can be positioned inside the patient's vasculature to face and/or contact the tissue of the main pulmonary artery, the left pulmonary artery and/or the right pulmonary artery. When the one or more electrodes 114 are in contact with luminal surface of the patient's vasculature, the one or more electrodes 114 will be pointing away from the majority of the blood volume of that region of the pulmonary artery. This allows the electrical pulses from the one or more electrodes 114 to be directed into the tissue adjacent the implant location, instead of being directed into the blood volume.

The exposed face 118 of the one or more electrodes 114 can have a variety of shapes. For example, the exposed face 118 can have a flat planar shape. In this embodiment, the exposed face 118 of the electrodes 114 can be co-planar with the one surface of the three or more surfaces 112 of the elongate body 102. In an alternative embodiment, the exposed face 118 of the electrodes 114 can have a semi-hemispherical shape. Other shapes for the exposed face 118 of the electrodes 114 can include semi-cylindrical, wave-shaped, and zig-zag-shaped. The exposed face 118 of the electrodes 114 can also include one or more anchor structures. Examples of such anchor structures include hooks that can optionally include a barb. Similarly, the electrodes can be shaped to also act as anchor structures.

In an additional embodiment, the one surface of the three or more surfaces 112 of the elongate body 102 that include the exposed face 118 of the one or more electrodes 114 can further include anchor structures 120 that extend above the one surface of the three or more surfaces 112. As illustrated, the anchor structures 120 can include portions that can contact the vascular tissue in such a way that the movement of the one or more electrodes 114 at the location where they contact the vascular tissue is minimized. The anchor structures 120 can have a variety of shapes that may help to achieve this goal. For example, the anchor structures 120 can have a conical shape, where the vertex of the conical shape can contact the vascular tissue. In an additional embodiment, the anchor structures 120 can have a hook configuration (with or without a barb).

As illustrated, the elongate body 102 of catheter 100 can also include a portion 122 with a circular cross-section shape taken perpendicularly to the longitudinal center axis 108. The elongate body 102 of catheter 100 also includes a surface 124 defining a guide-wire lumen 126 that extends through the elongate body 102. The guide-wire lumen 126 has a diameter that is sufficiently large to allow the guide wire to freely pass through the guide-wire lumen 126. The guide-wire lumen 126 can be positioned concentrically relative the longitudinal center axis 108 of the elongate body 102.

Alternatively, and as illustrated in FIG. 1, the guide-wire lumen 126 is positioned eccentrically relative the longitudinal center axis 108 of the elongate body 102. When the guide-wire lumen 126 is positioned eccentrically relative the longitudinal center axis 108 the guide-wire lumen 126 will have a wall thickness 128 taken perpendicularly to the longitudinal center axis that is greater than a wall thickness 130 of a remainder of the catheter taken perpendicularly to the longitudinal center axis. For this configuration, the differences in wall thickness 128 and 130 help to provide the elongate body 102 with a preferential direction in which to bend. For example, the wall thickness 128 of the elongate body 102 being greater than the wall thickness 130 will cause the side of the elongate body 102 with the greater wall thickness to preferentially have the larger radius of curvature when the elongate body 102 bends. By positioning the exposed face 118 of the electrodes 114 on the side of the elongate body 102 having the great wall thickness (e.g., wall thickness 128), the one or more electrodes 114 can be more easily and predictably brought into contact with the luminal surface of the vasculature in and around the main pulmonary artery and at least one of the pulmonary arteries.

The catheter 100 shown in FIG. 1 can be positioned in the main pulmonary artery and/or one or both of the pulmonary arteries of the patient, as described herein. To accomplish this, a pulmonary artery guide catheter is introduced into the vasculature through a percutaneous incision and guided to the right ventricle using known techniques. For example, the pulmonary artery guide catheter can be inserted into the vasculature via a peripheral vein of the arm (e.g., as with a peripherally inserted central catheter). Other approaches can include, but are not limited to, an Internal Jugular approach, as is known. Changes in a patient's electrocardiography and/or pressure signals from the vasculature can be used to guide and locate the pulmonary artery guide catheter within the patient's heart. Once in the proper location, a guide wire can be introduced into the patient via the pulmonary artery guide catheter, where the guide wire is advanced into the main pulmonary artery and/or one of the pulmonary arteries. Using the guide-wire lumen 126, the catheter 100 can be advanced over the guide wire so as to position the catheter 100 in the main pulmonary artery and/or one or both of the pulmonary arteries of the patient, as described herein. Various imaging modalities can be used in positioning the guide wire of the present disclosure in the main pulmonary artery and/or one of the pulmonary arteries of the patient. Such imaging modalities include, but are not limited to, fluoroscopy, ultrasound, electromagnetic, electropotential modalities.

Using a stimulation system, as discussed herein, stimulation electrical energy can be delivered across combinations of one or more of the electrodes 114. It is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the patient.

Figure 2:
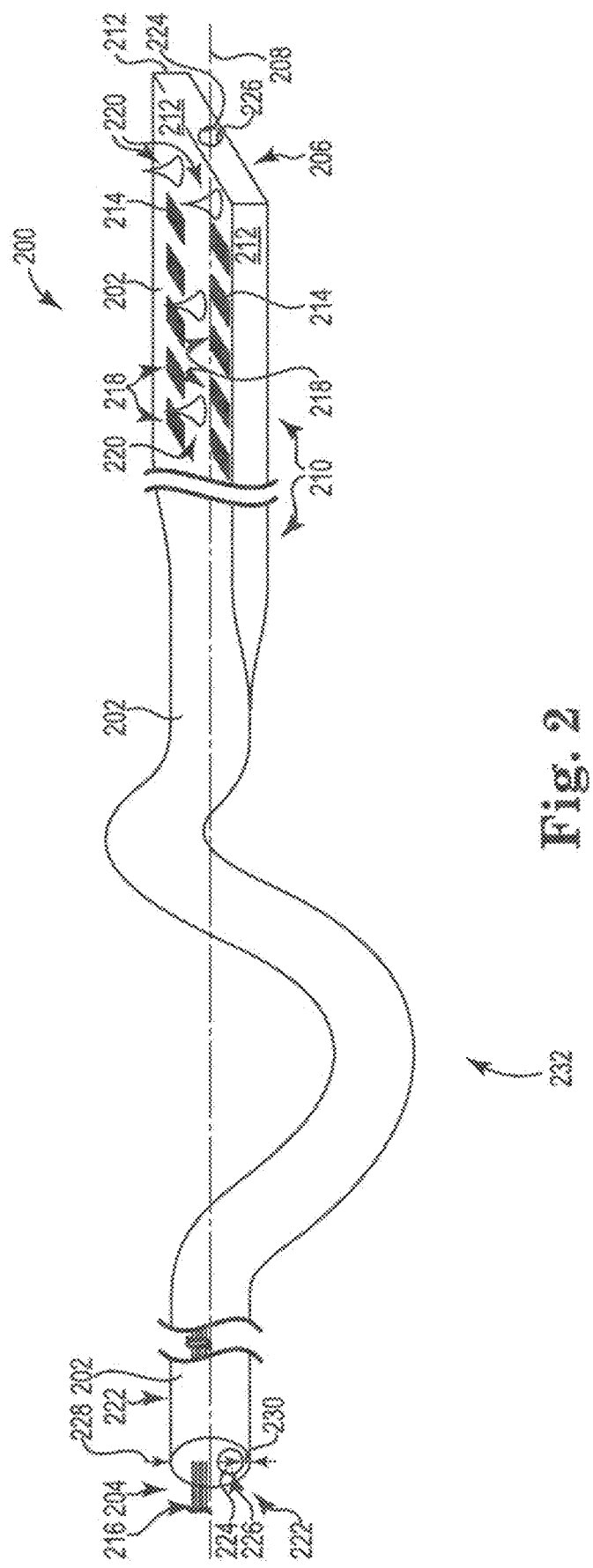
FIG. 2 provides an illustration of an embodiment of the catheter according to the present disclosure.

FIG. 2 provides an additional embodiment of the catheter 200 as provided herein. The catheter 200 includes the features and components as discussed above, a discussion of which is not repeated but the element numbers are included in FIG. 2 with the understanding that the discussion of these elements is implicit. In addition, the elongate body 202 of the catheter 200 includes a serpentine portion 232 proximal to the one or more electrodes 214. When implanted in the vasculature of the patient, the serpentine portion 232 of the elongate body 202 can act as a "spring" to absorb and isolate the movement of the one or more electrodes 214 from the remainder of the elongate body 202 of the catheter 200. Besides having a serpentine shape, the serpentine portion 232 can have a coil like configuration. Other shapes that achieve the objective of absorbing and isolating the movement of the one or more electrodes 214 from the remainder of the elongate body 202 of the catheter 200 once implanted are possible. During delivery of the catheter 200, the presences of the guide wire in the guide-wire lumen 226 can help to temporarily straighten the serpentine portion 232 of the elongate body 202.

Figure 3:
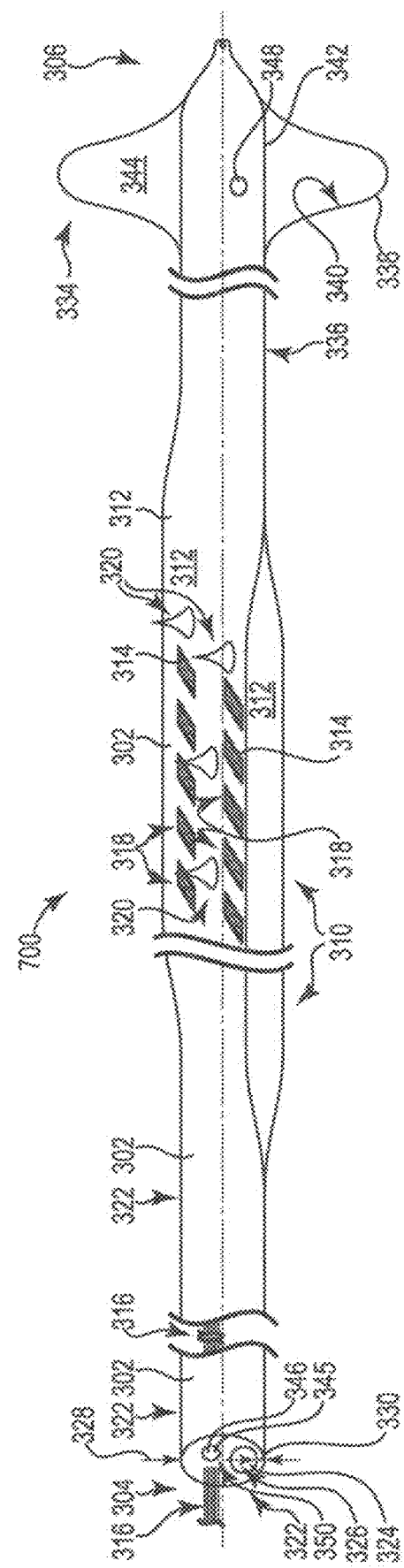
FIG. 3 provides an illustration of an embodiment of the catheter according to the present disclosure.

Referring now to FIG. 3 there is shown an additional embodiment of the catheter 300 as provided herein. The catheter 300 can include the features and components as discussed above for catheters 100 and/or 200, a discussion of which is not repeated but the element numbers are included in FIG. 3 with the understanding that the discussion of these elements is implicit. In addition, the catheter 300 of the present embodiment includes an inflatable balloon 334. As illustrated, the elongate body 302 includes a peripheral surface 336, where the inflatable balloon 334 is located on the peripheral surface 336 of the elongate body 302. The inflatable balloon 334 includes a balloon wall 338 with an interior surface 340 that along with a portion 342 of the peripheral surface 336 of the elongate body 302 defines a fluid tight volume 344.

The elongate body 302 further includes a surface 345 that defines an inflation lumen 346 that extends through the elongate body 302. The inflation lumen 346 includes a first opening 348 into the fluid tight volume 344 of the inflatable balloon 334 and a second opening 350 proximal to the first opening 348 to allow for a fluid to move in the fluid tight volume 344 to inflate and deflate the balloon 334. A syringe, or other known devices, containing the fluid (e.g., saline or a gas (e.g., oxygen)) can be used to inflate and deflate the balloon 334.

The catheter 300 shown in FIG. 3 can positioned in the main pulmonary artery and/or one or both of the pulmonary arteries of the patient, as described herein. As discussed herein, a pulmonary artery guide catheter is introduced into the vasculature through a percutaneous incision, and guided to the right ventricle using known techniques. Once in the proper location, the balloon 334 can be inflated, as described, to allow the catheter 300 to be carried by the flow of blood from the right ventricle to the main pulmonary artery and/or one of the pulmonary arteries. Additionally, various imaging modalities can be used in positioning the catheter of the present disclosure in the main pulmonary artery and/or one of the pulmonary arteries of the patient. Such imaging modalities include, but are not limited to, fluoroscopy, ultrasound, electromagnetic, electropotential modalities.

The catheter 300 can be advance along the main pulmonary artery until the second end 306 of the catheter 300 contacts the top of the main pulmonary artery (e.g., a location distal to the pulmonary valve and adjacent to both the pulmonary arteries). Once the second end 306 of the catheter 300 reaches the top of the main pulmonary artery the pulmonary artery guide catheter can be moved relative the catheter 300 so as to deploy the catheter 300 from the pulmonary artery guide catheter.

Markings can be present on the peripheral surface of the catheter body 302, where the markings start and extend from the first end 302 towards the second end 306 of the catheter body 302. The distance between the markings can be of units (e.g., millimeters, inches, etc.), which can allow the length between the second end 306 of the catheter 300 and the top of the main pulmonary artery to be determined.

The ability to measure this distance from the top of the main pulmonary artery may be helpful in placing the one or more electrodes 314 in a desired location within the main pulmonary artery. In addition to measuring the distance from which the second end 306 of the elongate body 302 is placed from the top of the main pulmonary artery, the elongate body 302 can also be used to identify, or map, an optimal position for the one or more electrodes 314 within the vasculature. For example, the second end 306 of the elongate body 302 can be positioned at the desired distance from the top of the main pulmonary artery using the markings on the peripheral surface of the catheter body 302.

Using the stimulation system, as discussed herein, stimulation electrical energy can be delivered across combinations of the one or more electrodes 314. It is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the patient.

Figure 4:
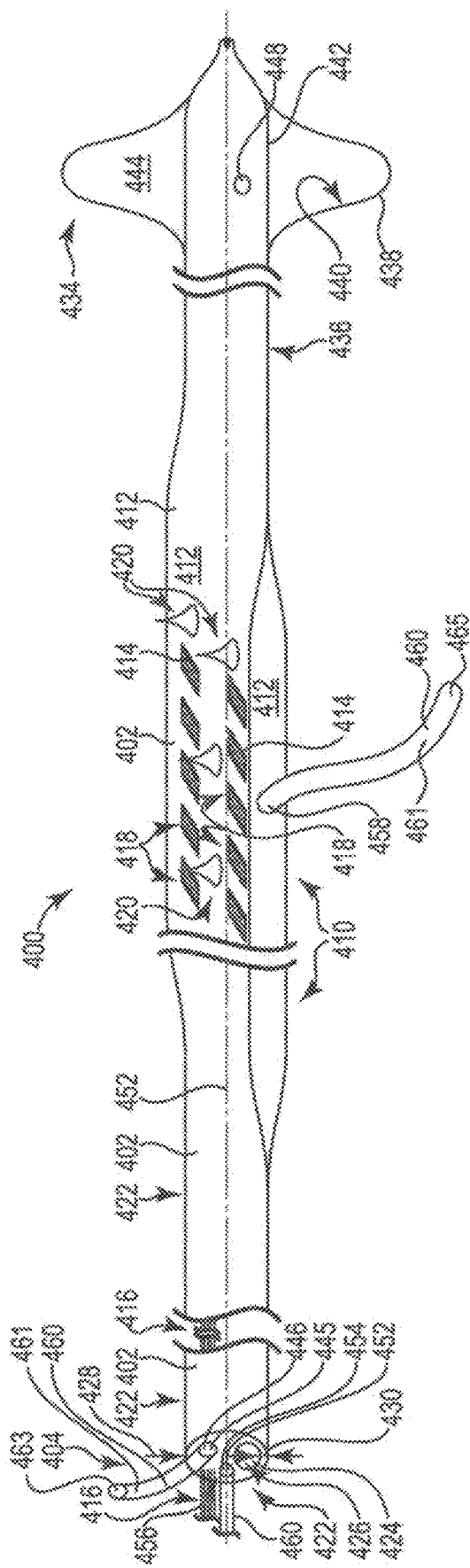
FIG. 4 provides an illustration of an embodiment of the catheter according to the present disclosure.

Referring now to FIG. 4 there is shown an additional embodiment of the catheter 400 as according to the present disclosure. The catheter 400 can include the features and components as discussed above for catheters 100, 200 and/or 300, a discussion of which is not repeated but the element numbers are included in FIG. 4 with the understanding that the discussion of these elements is implicit. In addition, the catheter 400 of the present embodiment includes a surface 452 defining a deflection lumen 454. The deflection lumen 454 includes a first opening 456 and a second opening 458 in the elongate body 402. In one embodiment, the second opening 458 can be opposite the one or more electrodes 414 on one surface of the three or more surfaces 412 of the elongate body 402.

The catheter 400 further includes an elongate deflection member 460. The elongate deflection member 460 includes an elongate body 461 having a first end 463 and a second end 465. The elongate deflection member 460 extends through the first opening 456 to the second opening 458 of the deflection lumen 454. The deflection lumen 454 has a size (e.g., a diameter) sufficient to allow the deflection member 460 to pass through the deflection lumen 454 with the first end 463 of the deflection member 460 proximal to the first end 404 of the elongate body 402 and the second end 465 of the deflection member 460 extendable from the second opening 458 of the deflection lumen 454. Pressure applied from the first end 463 of the deflection member 460 can cause the deflection member 460 to move within the deflection lumen 454. For example, when pressure is applied to the deflection member 460 to move the first end 463 of the deflection member 460 towards the first opening 456 of the deflection lumen 454, the pressure causes the second end 465 of the deflection member 460 to extend from the second opening 458.

As generally illustrated, the elongate deflection member 460 can be advanced through the deflection lumen 454 so that elongate deflection member 460 extends laterally away from the one or more electrodes 414 on the one surface of the three or more surfaces 412 of the elongate body 402. The elongate deflection member 460 can be of a length and shape that allows the elongate deflection member 460 to be extended a distance sufficient to bring the one or more electrodes 414 into contact with the vascular luminal surface (e.g., a posterior surface of the main pulmonary artery and/or one or both of the pulmonary arteries) with a variety of pressures. Optionally, the elongate deflection member 460 can be configured to include one or more of the electrode 414, as discussed herein.

For the various embodiments, the elongate body 461 of the deflection member 460 is formed of a flexible polymeric material. Examples of such flexible polymeric material include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

In an additional embodiment, the elongate body 461 of the elongate deflection member 460 can also include one or more support wires. The support wires can be encased in the flexible polymeric material of the elongate body 461, where the support wires can help to provide both column strength and a predefined shape to the elongate deflection member 460. For example, the support wires can have a coil shape that extends longitudinally along the length of the elongate body 461. The coil shape allows for the longitudinal force applied near or at the first end 463 of the deflection member 460 to be transferred through the elongate body 461 so as to laterally extend the second end 465 of the deflection member 460 from the second opening 458 of the deflection lumen 454.

The support wires can also provide the deflection member 460 with a predetermined shape upon laterally extending from the second opening 458 of the deflection lumen 454. The predetermined shape can be determined to engage the luminal wall of the pulmonary artery in order to bring the electrodes 414 into contact with the vascular tissue. The predetermined shape and the support wires can also help to impart stiffness to the deflection member 460 that is sufficient to maintain the electrodes 414 on the luminal wall of the pulmonary artery under the conditions within the vasculature of the patient.

The support wires can be formed of a variety of metals or metal alloys. Examples of such metals or metal alloys include surgical grade stainless steel, such as austenitic 316 stainless among others, and the nickel and titanium alloy known as Nitinol. Other metals and/or metal alloys, as are known, can be used.

The catheter 400 shown in FIG. 4 can positioned in the main pulmonary artery and/or one or both of the pulmonary arteries of the patient, as described herein. As discussed herein, a pulmonary artery guide catheter is introduced into the vasculature through a percutaneous incision, and guided to the right ventricle using known techniques. Once in the proper location, the balloon 434 can be inflated, as described, to allow the catheter 400 to be carried by the flow of blood from the right ventricle to the main pulmonary artery and/or one of the pulmonary arteries. Additionally, various imaging modalities can be used in positioning the catheter of the present disclosure in the main pulmonary artery and/or one of the pulmonary arteries of the patient. Such imaging modalities include, but are not limited to, fluoroscopy, ultrasound, electromagnetic, electropotential modalities.

The catheter 400 can be advance along the main pulmonary artery until the second end 406 of the catheter 400 contacts the top of the main pulmonary artery (e.g., a location distal to the pulmonary valve and adjacent to both the pulmonary arteries). Once the second end 406 of the catheter 400 reaches the top of the main pulmonary artery the pulmonary artery guide catheter can be moved relative the catheter 400 so as to deploy the catheter 400 from the pulmonary artery guide catheter.

Markings, as discussed herein, can be present on the peripheral surface of the catheter body 402 that can assist in positioning the catheter 400 within the main pulmonary artery.

The ability to measure this distance from the top of the main pulmonary artery may be helpful in placing the one or more electrodes 414 in a desired location within the main pulmonary artery. In addition to measuring the distance from which the second end 406 of the elongate body 402 is placed from the top of the main pulmonary artery, the elongate body 402 can also be used to identify, or map, an optimal position for the one or more electrodes 414 within the vasculature. For example, the second end 406 of the elongate body 402 can be positioned at the desired distance from the top of the main pulmonary artery using the markings on the peripheral surface of the catheter body 402.

When desired, the elongate deflection member 460 can be extended laterally from the elongate body 402 to a distance sufficient to cause the one surface of the three or more surfaces 412 of the elongate body 402 having the one or more electrodes to contact a surface of the main pulmonary artery, such as the anterior surface of the main pulmonary artery, and thereby bring the one or more electrodes 414 into contact with the main pulmonary artery or one of the pulmonary arteries (the left pulmonary artery or the right pulmonary artery). The elongate deflection member 460, as will be appreciated, biases and helps to place the one or more electrodes 414 along the vessel surface (e.g., along the posterior surface of the main pulmonary artery or one of the pulmonary arteries (the left pulmonary artery or the right pulmonary artery)).

Due to its adjustable nature (e.g., how much pressure is applied to the elongate deflection member 460), the elongate deflection member 460 can be used to bring the one or more electrodes 414 into contact with the luminal surface of the main pulmonary artery or one of the pulmonary arteries with a variety of pressures. So, for example, the elongate deflection member 460 can bring the one or more electrodes 414 into contact with the luminal surface of the main pulmonary artery or one of the pulmonary arteries with a first pressure. Using the stimulation system, as discussed herein, stimulation electrical energy can be delivered across combinations of the one or more electrodes 414 in the electrode array. It is possible for the patient's cardiac response to the stimulation electrical energy to be monitored and recorded for comparison to other subsequent tests.

It is appreciated that for any of the catheters discussed herein any combination of electrodes, including reference electrodes (as discussed herein) positioned within or on the patient's body, can be used in providing stimulation to and sensing cardiac signals from the patient.

If necessary, the distance the elongate deflection member 460 extends laterally from the elongate body 402 can be changed (e.g., made shorter) to allow the elongate body 402 to be rotated in either a clockwise or counter-clockwise direction, thereby repositioning the one or more electrodes 414 in contact with the luminal surface of the main pulmonary artery or one of the pulmonary arteries. The stimulation system can again be used to deliver stimulation electrical energy across combinations of one or more of the electrodes 414 in the electrode array. The patient's cardiac response to this subsequent test can then be monitored and recorded for comparison to previous and subsequent test. In this way, a preferred location for the position of the one or more electrodes 414 along the luminal surface of the main pulmonary artery or one of the pulmonary arteries can be identified. Once identified, the elongate deflection member 460 can be used to increase the lateral pressure applied to the one or more electrodes, thereby helping to better anchor the catheter 400 in the patient.

Figure 5:
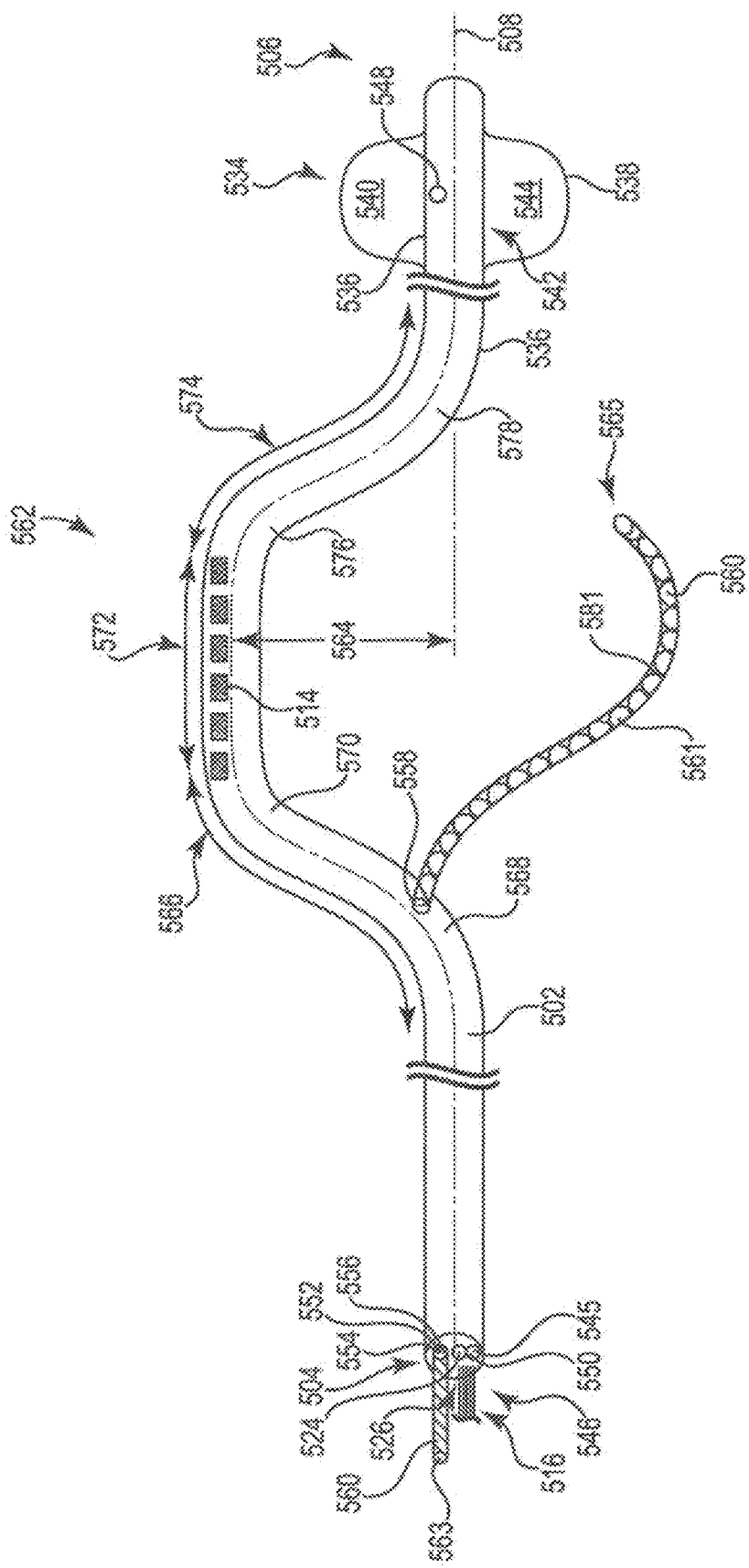
FIG. 5 provides an illustration of an embodiment of the catheter according to the present disclosure.

Referring now to FIG. 5, there is shown an additional embodiment of a catheter 562. The catheter 562 includes an elongate body 502 having a peripheral surface 536 and a longitudinal center axis 508 extending between a first end 504 and a second end 506. The catheter 562 can include the features and components as discussed above for catheters 100, 200, 300 and/or 400, a discussion of which is not repeated but the element numbers are included in FIG. 5 with the understanding that the discussion of these elements is implicit.

The catheter 562 of the present embodiment includes an inflatable balloon 534. As illustrated, the elongate body 502 includes a peripheral surface 536, where the inflatable balloon 534 is located on the peripheral surface 536 of the elongate body 502. The inflatable balloon 534 includes a balloon wall 538 with an interior surface 540 that along with a portion 542 of the peripheral surface 536 of the elongate body 502 defines a fluid tight volume 544.

The elongate body 502 further includes a surface 545 that defines an inflation lumen 546 that extends through the elongate body 502. The inflation lumen 546 includes a first opening 548 into the fluid tight volume 544 of the inflatable balloon 534 and a second opening 550 proximal to the first opening 548 to allow for a fluid to move in the fluid tight volume 544 to inflate and deflate the balloon 534. A syringe, or other known devices, containing the fluid (e.g., saline or a gas (e.g., oxygen)) can be used to inflate and deflate the balloon 534.

The elongate body 502 further includes an offset region 564 defined by a series of predefined curves along the longitudinal center axis 508. As used herein, "predefined curves" are curves formed in the elongate body 502 during the production of the catheter 562, where when deformed such curves provide a spring like force to return to their pre-deformation shape (i.e., their original shape). As illustrated, the series of predefined curves includes a first portion 566 that has a first curve 568 in the longitudinal center axis 508 followed by a second curve 570 in the longitudinal center axis 508 of the elongate body 502. The length and degree of each of the first curve 568 and second curve 570, along with the distance between such curves helps to define the height of the offset region 564. As discussed herein, the height of the offset region 564 can be determined by the inner diameter of one or more locations along the main pulmonary artery and/or one of the pulmonary arteries.

The first portion 566 of the elongate body 502 is followed by a second portion 572 of the elongate body 502. The longitudinal center axis 508 along the second portion 572 can have a zero curvature (i.e., a straight line), as illustrated in FIG. 5. The second portion 572 of the elongate body 502 is followed by a third portion 574 of the elongate body 502. The longitudinal center axis 508 transitions from the second portion 572 along a third curve 576, which then transitions into a fourth curve 578. As illustrated, after the fourth curve 578, the longitudinal center axis 508 is approximately co-linear with the longitudinal center axis 508 leading up to the first curve 568. It is noted that the curves of the first portion 566 and the second portion 574 can also all be in approximately the same plane. It is, however, possible that the curves of the first portion 566 and the second portion 574 are not in the same plane. For example, when the curves of the first portion 566 and the second portion 574 are not in the same plane the longitudinal center axis 508 can include a helical curve through these portions of the elongate body 502. Other shapes are possible.

The elongate body 502 can further include one or more electrodes 514, as discussed herein, along the second portion 572 of the offset region 564 of the elongate body 502. As illustrated, the one or more electrodes 514 can be on the surface of the elongate body 502 in the second portion 572 of the offset region 564. Conductive elements 516 extend through the elongate body 502, where the conductive elements 516 can be used, as discussed herein, to conduct electrical current to combinations of the one or more electrodes 514. Each of the one or more electrodes 514 is coupled to a corresponding conductive element 516. The conductive elements 516 are electrically isolated from each other and extend through the elongate body 502 from each respective electrode 514 through the first end 504 of the elongate body 502. The conductive elements 516 terminate at a connector port, where each of the conductive elements 516 can be releasably coupled to a stimulation system, as discussed herein. It is also possible that the conductive elements 516 are permanently coupled to the stimulation system (e.g., not releasably coupled). The stimulation system can be used to provide stimulation electrical energy that is conducted through the conductive elements 516 and delivered across combinations of the one or more electrodes 514. The one or more electrodes 514 are electrically isolated from one another, where the elongate body 502 is formed of an electrically insulating material as discussed herein.

There can be wide variety for the number and configuration of the one or more electrodes 514 on the one surface of the second portion 572 of the elongate body 502. For example, as illustrated, the one or more electrodes 514 can be configured as an array of electrodes, where the number of electrodes and their relative position to each other can vary depending upon the desired implant location. As discussed herein, the one or more electrodes 514 can be configured to allow for electrical current to be delivered from and/or between different combinations of the one or more electrodes 514. The electrodes in the array of electrodes can have a repeating pattern where the electrodes are equally spaced from each other. So, for example, the electrodes in the array of electrodes can have a column and row configuration. Alternatively, the electrodes in the array of electrodes can have a concentric radial pattern, where the electrodes are positioned so as to form concentric rings of the electrodes. Other patterns are possible, where such patterns can either be repeating patterns or random patterns. As discussed herein, the catheter 562 further includes conductive elements 516 extending through the elongate body, where the conductive elements 516 conduct electrical current to combinations of the one or more electrodes 514.

As discussed herein, the length and degree of each of the curves, along with the distance between such curves, helping to define the first portion 566 and the third portion 574 of the longitudinal center axis 508 helps to define the relative height of the offset region 564. For the various embodiments, the height of the offset region 564 can be determined by the inner diameter of one or more locations along the main pulmonary artery and/or one of the pulmonary arteries. In this way the first portion 566 and the third portion 574 can bring the second portion 572 and the one or more electrodes 514 on the surface of the elongate body 502 into contact with the vascular wall of the patient in the main pulmonary artery and/or one of the pulmonary arteries. In other words, the transitions of the first portion 566 and the third portion 574 of the elongate body 502 in the offset region 564 can act to bias the second portion 572 and the one or more electrodes 514 against the vascular wall of the patient in the main pulmonary artery and/or one of the pulmonary arteries.

The elongate body 502 further includes a surface 524 defining a guide-wire lumen 526 that extends through the elongate body 502. As provided herein, the guide-wire lumen 526 can be concentric relative the longitudinal center axis 508 of the elongate body 502 (as illustrated in FIG. 5). Alternatively, the guide-wire lumen 526 can be eccentric relative the longitudinal center axis 508 of the elongate body 502. As discussed herein, the guide-wire lumen 526 can have a wall thickness 528 that is greater than a wall thickness 530 of a remainder of the catheter 562 taken perpendicularly to the longitudinal center axis 508. In an additional embodiment, a portion of the elongate body 502 includes a serpentine portion, as discussed and illustrated herein, proximal to the one or more electrodes 514.

For the present embodiment, a guide-wire used with the catheter 562 can serve to temporarily "straighten" the offset region 564 when the guide-wire is present in the guide-wire lumen 526 that passes along the offset region 564. Alternatively, the guide-wire can be used to impart the shape of the offset region 564 to the catheter 562. In this embodiment, the elongate body 502 of the catheter 562 can have a straight shape (e.g., no predefined lateral shape). To impart the offset region 564 the guide wire is "shaped" (e.g., bent) to the desired configuration of the offset region at point that corresponds to the desired longitudinal location for the offset region on the elongate body 502. The offset region 564 of the catheter 562 can be provided by inserting the guide wire with the predefined lateral shape.

In FIG. 5 the catheter 562 of the present embodiment further includes a surface 552 defining a deflection lumen 554, as discussed herein. The catheter 562 further includes an elongate deflection member 560, also as discussed herein. As generally illustrated, the elongate deflection member 560 can be advanced through the deflection lumen 554 so that elongate deflection member 560 extends laterally away from the one or more electrodes 514 on the second portion 572 of the elongate body 502. The elongate deflection member 560 can be of a length and shape that allows the elongate deflection member 560 to be extended a distance sufficient to bring the one or more electrodes 514 into contact with the vascular luminal surface (e.g., a posterior surface of the main pulmonary artery and/or one or both of the pulmonary arteries) with a variety of pressures.

In an additional embodiment, the elongate body 561 of the elongate deflection member 560 can also include one or more support wires 581. The support wires 581 can be encased in the flexible polymeric material of the elongate body 561, where the support wires 581 can help to provide both column strength and a predefined shape to the elongate deflection member 560. For example, the support wires 581 can have a coil shape that extends longitudinally along the length of the elongate body 561. The coil shape allows for the longitudinal force applied near or at the first end 563 of the deflection member 560 to be transferred through the elongate body 561 so as to laterally extend the second end 565 of the deflection member 560 from the second opening 558 of the deflection lumen 554.

The support wires 581 can also provide the deflection member 560 with a predetermined shape upon laterally extending from the second opening 558 of the deflection lumen 554. The predetermined shape can be determined to engage the luminal wall of the pulmonary artery in order to bring the electrodes 514 on the second portion 572 of the offset region 564 into contact with the vascular tissue. The predetermined shape and the support wires 581 can also help to impart stiffness to the deflection member 560 that is sufficient to maintain the electrodes 514 on the luminal wall of the pulmonary artery under the conditions within the vasculature of the patient.

The support wires 581 can be formed of a variety of metals or metal alloys. Examples of such metals or metal alloys include surgical grade stainless steel, such as austenitic 316 stainless among others, and the nickel and titanium alloy known as Nitinol. Other metals and/or metal alloys, as are known, can be used.

Figure 6:
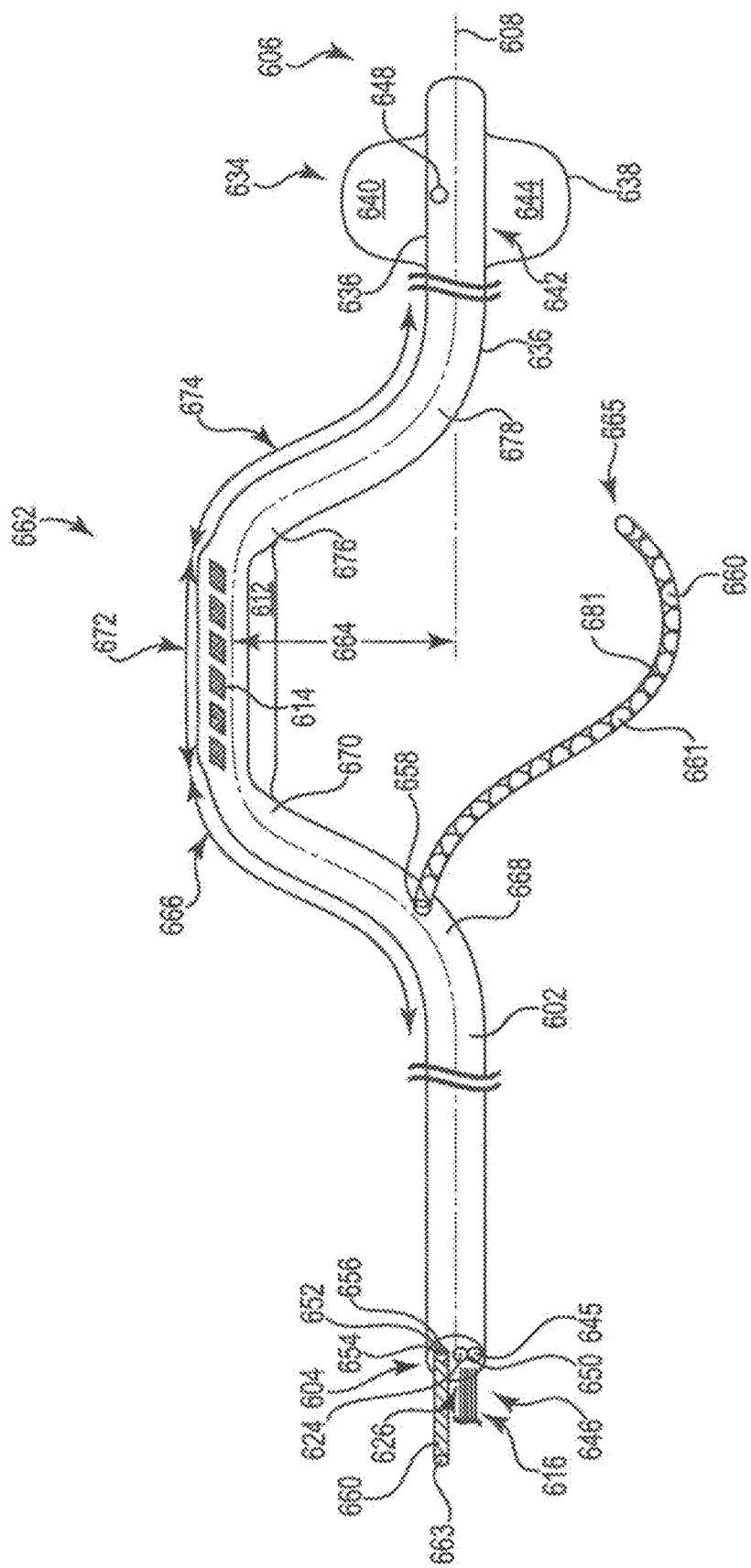
FIG. 6 provides an illustration of an embodiment of the catheter according to the present disclosure.

Referring now to FIG. 6, there is shown an additional embodiment of a catheter 662 according to the present disclosure. The catheter 662 can include the features and components as discussed above for catheters 100, 200, 300, 400 and/or 500, a discussion of which is not repeated but the element numbers are included in FIG. 6 with the understanding that the discussion of these elements is implicit.

The catheter 662 seen in FIG. 6 is similar to the catheter 562 of FIG. 5, where the elongate body 602 of catheter 662 further includes three or more surfaces 612 defining a convex polygonal cross-sectional shape taken perpendicularly to the longitudinal center axis 608, as discussed for the catheters 100, 200, 300 and 400 herein. As illustrated, the one or more electrodes 614 are on one surface of the three or more surfaces 612 of the elongate body 602. In the present embodiment, the three or more surfaces 612 of the elongate body 602 help to form the second portion 672 of the elongate body 602. If desired, the elongate body 602 can includes a serpentine portion proximal to the one or more electrodes 614.

Figure 7:
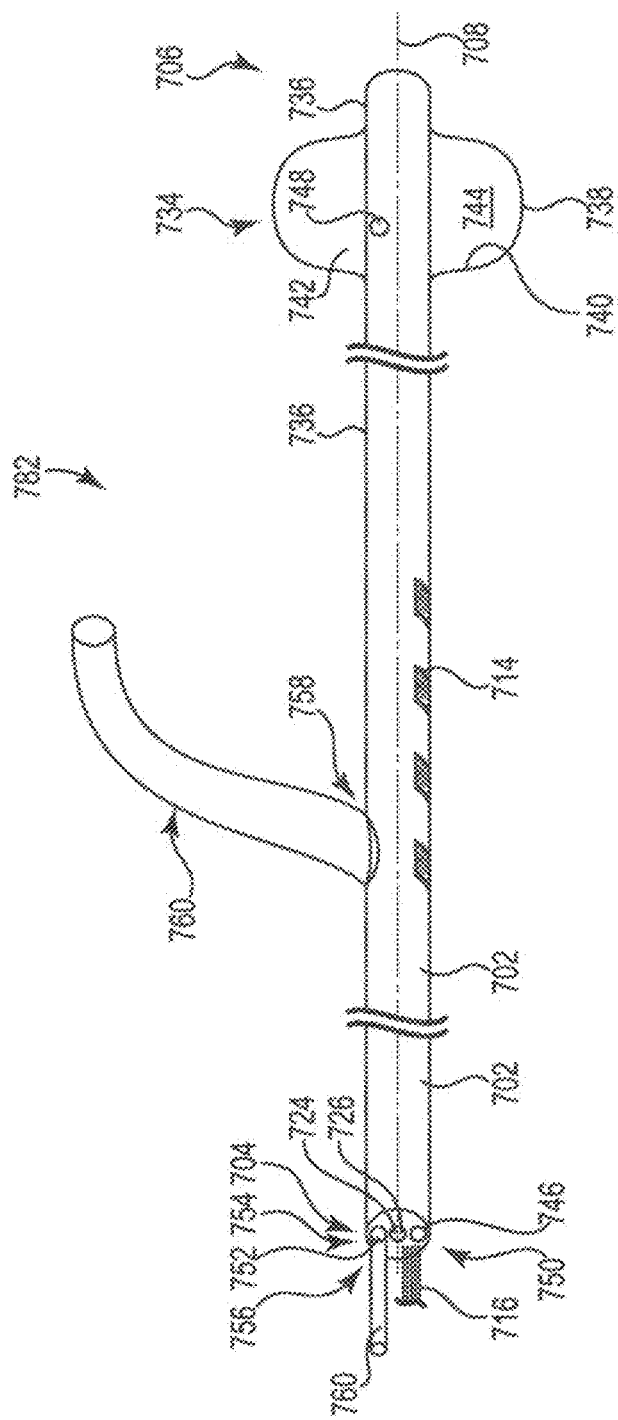
FIG. 7 provides an illustration of an embodiment of the catheter according to the present disclosure.

Referring now to FIG. 7, there is shown an additional embodiment of a catheter 782 according to the present disclosure. The catheter 782 can include the features and components as discussed above for catheters 100, 200, 300, 400, 500 and/or 600, a discussion of which is not repeated but the element numbers are included in FIG. 7 with the understanding that the discussion of these elements is implicit.

The catheter 782 includes an elongate body 702 having a peripheral surface 736 and a longitudinal center axis 708 extending between a first end 704 and a second end 706. The elongate body 702 includes a surface 752 defining a deflection lumen 754, where the deflection lumen 754 includes a first opening 756 and a second opening 758 in the elongate body 702. The catheter 782 further includes an inflatable balloon 734 on the peripheral surface 736 of the elongate body 702, the inflatable balloon 734 having a balloon wall 738 with an interior surface 740 that along with a portion 742 of the peripheral surface 736 of the elongate body 702 defines a fluid tight volume 744, as discussed herein. An inflation lumen 746 extends through the elongate body 702, where the inflation lumen 746 has a first opening 748 into the fluid tight volume 744 of the inflatable balloon 734 and a second opening 750 proximal to the first opening 748 to allow for a fluid to move in the fluid tight volume 744 to inflate and deflate the balloon 734.

One or more electrodes 714 are on the elongate body 702, where the second opening 758 of the deflection lumen 754 is opposite the one or more electrodes 714 on the elongate body 702. The catheter 782 further includes an elongate deflection member 760, as discussed herein, where the elongate deflection member 760 extends through the second opening 758 of the deflection lumen 754 in a direction opposite the one or more electrodes 714 on one surface of the elongate body 702. The catheter 782 also includes conductive elements 716, as discussed herein, that extend through the elongate body 702, where the conductive elements 716 conduct electrical current to combinations of the one or more electrodes 714.

The catheter 782 further includes a surface 724 defining a guide-wire lumen 726 that extends through the elongate body 702. As illustrated, the guide-wire lumen 726 is concentric relative the longitudinal center axis 708. As discussed herein, the guide-wire lumen 726 could also be eccentric relative longitudinal center axis 708 of the elongate body 708. Such embodiments are discussed herein, where the guide-wire lumen 726 can have a wall thickness taken perpendicularly to the longitudinal center axis 708 that is greater than a wall thickness of a remainder of the catheter 782 taken perpendicularly to the longitudinal center axis 708. The catheter 782 can also include a serpentine portion of the elongate body 702 proximal to the one or more electrodes 714, as discussed herein.

Figure 8:
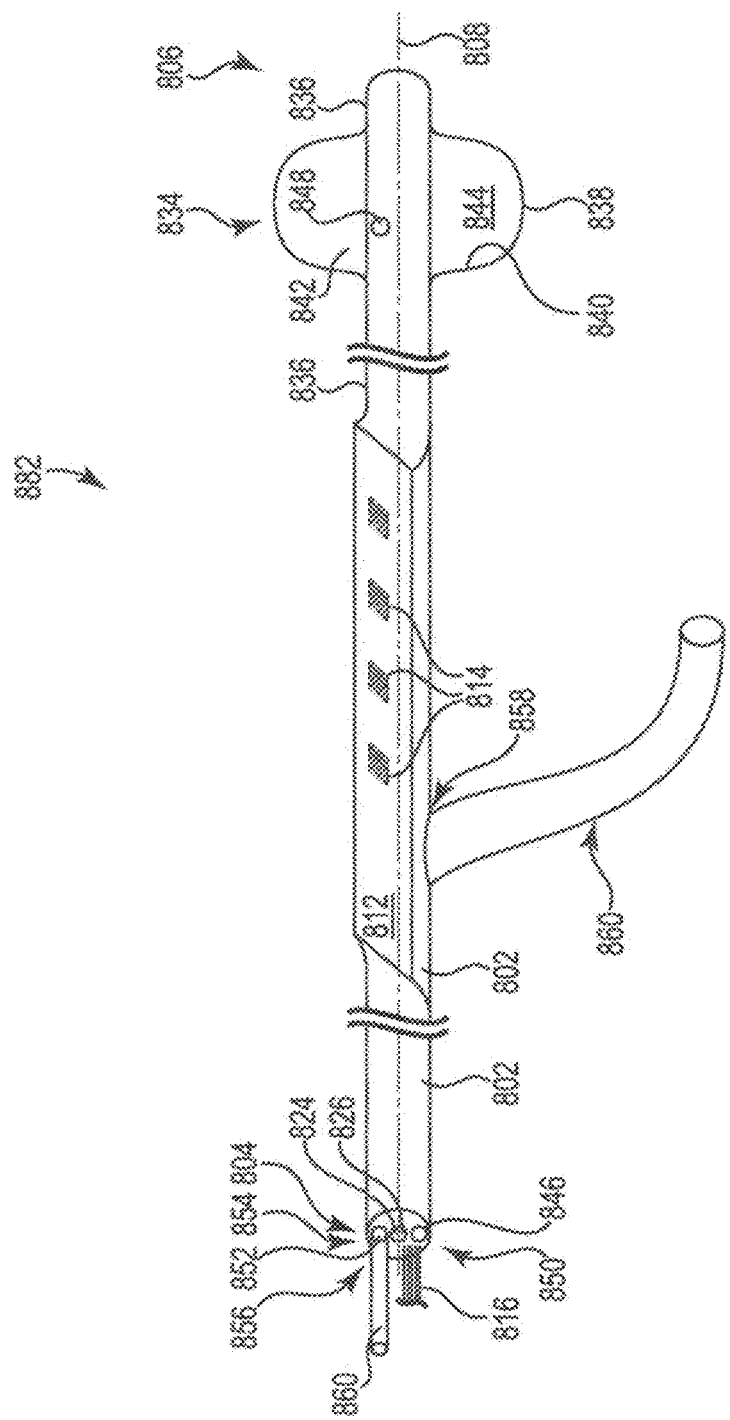
FIG. 8 provides an illustration of an embodiment of the catheter according to the present disclosure.

Referring now to FIG. 8, there is shown an additional embodiment of a catheter 882 according to the present disclosure. The catheter 882 can include the features and components as discussed above for catheters 100, 200, 300, 400, 500, 600 and/or 700, a discussion of which is not repeated but the element numbers are included in FIG. 8 with the understanding that the discussion of these elements is implicit.

The catheter 882 includes an elongate body 802 having a peripheral surface 836 and a longitudinal center axis 808 extending between a first end 804 and a second end 806. The elongate body 802 includes a surface 852 defining a deflection lumen 854, where the deflection lumen 854 includes a first opening 856 and a second opening 858 in the elongate body 802. The catheter 882 further includes an inflatable balloon 834 on the peripheral surface 836 of the elongate body 802, the inflatable balloon 834 having a balloon wall 838 with an interior surface 840 that along with a portion 842 of the peripheral surface 836 of the elongate body 802 defines a fluid tight volume 844, as discussed herein. An inflation lumen 846 extends through the elongate body 802, where the inflation lumen 846 has a first opening 848 into the fluid tight volume 844 of the inflatable balloon 834 and a second opening 850 proximal to the first opening 848 to allow for a fluid to move in the fluid tight volume 844 to inflate and deflate the balloon 834.

One or more electrodes 814 are on the elongate body 802, where the second opening 858 of the deflection lumen 854 is opposite the one or more electrodes 814 on the elongate body 802. As illustrated, the elongate body 802 has three or more surfaces 812 defining a convex polygonal cross-sectional shape taken perpendicularly to the longitudinal center axis 808. The one or more electrodes 814 are on one surface of the three or more surfaces 812 of the elongate body 802, as discussed herein.

The catheter 882 further includes an elongate deflection member 860, as discussed herein, where the elongate deflection member 860 extends through the second opening 858 of the deflection lumen 854 in a direction opposite the one or more electrodes 814 on one surface of the elongate body 802. The catheter 882 also includes conductive elements 816, as discussed herein, that extend through the elongate body 802, where the conductive elements 816 conduct electrical current to combinations of the one or more electrodes 814.

The catheter 882 further includes a surface 824 defining a guide-wire lumen 826 that extends through the elongate body 802. As illustrated, the guide-wire lumen 826 is concentric relative the longitudinal center axis 808. As discussed herein, the guide-wire lumen 826 could also be eccentric relative longitudinal center axis 808 of the elongate body 808. Such embodiments are discussed herein, where the guide-wire lumen 826 can have a wall thickness taken perpendicularly to the longitudinal center axis 808 that is greater than a wall thickness of a remainder of the catheter 882 taken perpendicularly to the longitudinal center axis 808. The catheter 882 can also include a serpentine portion of the elongate body 802 proximal to the one or more electrodes 814, as discussed herein.

Figure 9:
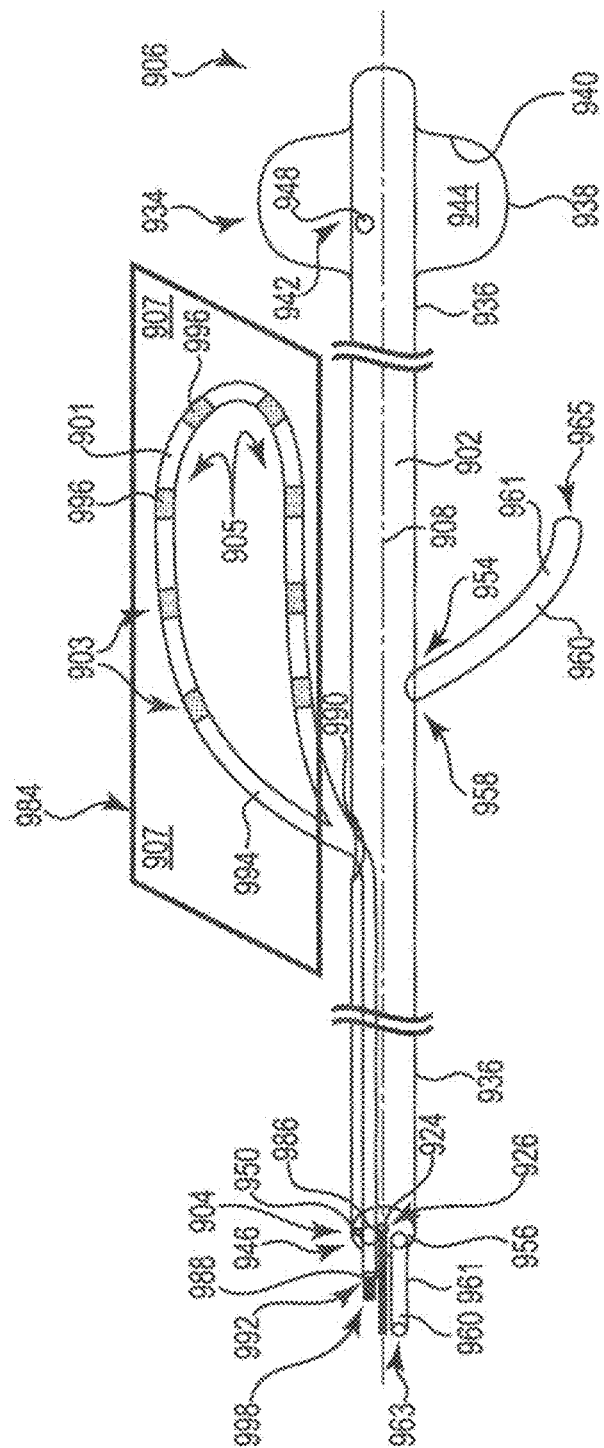
FIG. 9 provides an illustration of an embodiment of the catheter according to the present disclosure.

Referring now to FIG. 9, there is shown an additional embodiment of a catheter 984 according to the present disclosure. The catheter 984 can include the features and components as discussed above for catheters 100, 200, 300, 400, 500, 600, 700 and/or 800, a discussion of which is not repeated but the element numbers are included in FIG. 9 with the understanding that the discussion of these elements is implicit.

The catheter 984 includes an elongate body 902 having a peripheral surface 936 and a longitudinal center axis 908 extending between a first end 904 and a second end 906. The catheter 984 further includes an inflatable balloon 934 on the peripheral surface 936 of the elongate body 902, the inflatable balloon 934 having a balloon wall 938 with an interior surface 940 that along with a portion 942 of the peripheral surface 936 of the elongate body 902 defines a fluid tight volume 944, as discussed herein. An inflation lumen 946 extends through the elongate body 902, where the inflation lumen 946 has a first opening 948 into the fluid tight volume 944 of the inflatable balloon 934 and a second opening 950 proximal to the first opening 948 to allow for a fluid to move in the fluid tight volume 944 to inflate and deflate the balloon 934.

The catheter 982 includes a surface 924 defining a guide-wire lumen 926 that extends through the elongate body 902. As illustrated, the guide-wire lumen 926 is concentric relative the longitudinal center axis 908. As discussed herein, the guide-wire lumen 926 could also be eccentric relative longitudinal center axis 908 of the elongate body 908. Such embodiments are discussed herein, where the guide-wire lumen 926 can have a wall thickness taken perpendicularly to the longitudinal center axis 908 that is greater than a wall thickness of a remainder of the catheter 982 taken perpendicularly to the longitudinal center axis 908. The catheter 982 can also include a serpentine portion of the elongate body 902 proximal to the one or more electrodes 914, as discussed herein.

The elongate body 902 of the catheter 984 further includes a surface 986 defining an electrode lumen 988. The electrode lumen 988 includes a first opening 990 and a second opening 992 in the elongate body 902. The catheter 984 also includes an elongate electrode member 994, where the elongate electrode member 994 retractably extends through the first opening 990 of the electrode lumen 988 of the elongate body 902. The electrode lumen 988 has a size (e.g., a diameter) sufficient to allow the elongate electrode member 994 to pass through the electrode lumen 988 to that the elongate electrode member 994 can retractably extend through the first opening 990 of the electrode lumen 988 of the elongate body 902. The elongate electrode member 994 can retractably extend through the first opening 990 of the electrode lumen 988 of the elongate body 902 from pressure (e.g., compression or tension) applied by the user through the elongate electrode member 994 proximal to the second opening 992 in the elongate body 908. For the various embodiments, the elongate electrode member 994 is formed of a flexible polymeric material. Examples of such flexible polymeric material include, but are not limited to, those provided herein.

The elongate electrode member 994 includes one or more electrodes 996 and conductive elements 998 extending through the electrode lumen 988. As illustrated, the one or more electrodes 996 are on the surface 901 of the elongate electrode member 994. Conductive elements 998 extend through the elongate electrode member 994, where the conductive elements 998 can be used, as discussed herein, to conduct electrical current to combinations of the one or more electrodes 996. Each of the one or more electrodes 996 is coupled to a corresponding conductive element 998.

The conductive elements 998 are electrically isolated from each other and extend through the elongate electrode member 994 from each respective electrode 996 through the second end 992 of the electrode lumen 988. The conductive elements 998 terminate at a connector port, where each of the conductive elements 998 can be releasably coupled to a stimulation system, as discussed herein. It is also possible that the conductive elements 998 are permanently coupled to the stimulation system (e.g., not releasably coupled). The stimulation system can be used to conduct electrical current to combinations of the one or more electrodes 994 via the conductive elements 998. The one or more electrodes 996 are electrically isolated from one another, where the elongate electrode member 994 is formed of an electrically insulating material as discussed herein.

There can be a variety of the number and the configuration of the one or more electrodes 996 on the elongate electrode member 994. For example, as illustrated, the one or more electrodes 996 can be configured as an array of electrodes, where the number of electrodes and their relative position to each other can vary depending upon the desired implant location. As discussed herein, the one or more electrodes 996 can be configured to allow for electrical current to be delivered from and/or between different combinations of the one or more electrodes 996. So, for example, the electrodes in the array of electrodes can have a repeating pattern where the electrodes are equally spaced from each other. Other patterns are possible, where such patterns can either be repeating patterns or random patterns.

As illustrated, the one or more electrodes 996 have an exposed face 903. The exposed face 903 of the electrode 996 provides the opportunity for the electrode 996, when implanted in the patient, to be placed into proximity and/or in contact with the vascular tissue of the patient, as opposed to facing into the volume of blood in the artery. To accomplish this, the one or more electrodes 996 can be located on only one side of the elongate electrode member 994 (as illustrated in FIG. 9). This allows the one or more electrodes 996 to be brought into contact with the vascular luminal surface (e.g., a posterior surface of the main pulmonary artery and/or one or both of the pulmonary arteries). As the one or more electrodes 996 are located on only one side of the elongate electrode member 994, the electrodes 996 can be placed into direct proximity to and/or in contact with the tissue of any combination of the main pulmonary artery, the left pulmonary artery and/or the right pulmonary artery.

The exposed face 903 of the one or more electrodes 996 can have a variety of shapes, as discussed herein (e.g., a partial ring configuration, where each of the one or more electrodes 996 is positioned to face away from the elongate body 902). The exposed face 903 of the electrodes 996 can also include one or more anchor structures. Examples of such anchor structures include hooks that can optionally include a barb.

As generally illustrated, the elongate electrode member 994 can be advanced through the electrode lumen 988 so that the elongate electrode member 994 extends laterally away from the elongate body 908. The elongate electrode member 994 can be of a length and shape that allows the elongate electrode member 994 to be extended a distance sufficient from the elongate body 908 to bring the one or more electrodes 996 into contact with the vascular luminal surface (e.g., a posterior surface of the main pulmonary artery and/or one or both of the pulmonary arteries).

As illustrated in FIG. 9, the elongate electrode member 994 forms a loop 905 that extends away from the peripheral surface 936 of the elongate body 902. The loop 905 can have a variety of configurations relative the longitudinal axis 908 of the elongate body 902. For example, as illustrated in FIG. 9, the elongate electrode member 992 forming the loop 905 is in a plane 907 that is co-linear with the longitudinal center axis 908 of the elongate body 902.

The catheter 984 further includes an elongate deflection member 960, as previously discussed. As discussed herein, pressure is applied to the deflection member 960 to move the first end 963 of the deflection member 960 towards the first opening 956 of the deflection lumen 954. The pressure in addition to moving the first end 963 of the deflection member 960 towards the first opening 956 also causes the second end 965 of the deflection member 960 to extend from the second opening 958. As generally illustrated, the elongate deflection member 960 can be advanced through the deflection lumen 954 so that elongate deflection member 960 extends laterally away from the one or more electrodes 996 on the elongate electrode member 994. The elongate deflection member 960 can be of a length and shape that allows the elongate deflection member 960 to be extended a distance sufficient to help bring the one or more electrodes 996 into contact with the vascular luminal surface (e.g., a posterior surface of the main pulmonary artery and/or one or both of the pulmonary arteries) with a variety of pressures. Optionally, the elongate deflection member 960 can be configured to include one or more of the electrode, as discussed herein.

The catheter 984 shown in FIG. 9 can be positioned in the main pulmonary artery and/or one or both of the pulmonary arteries of the patient, as described herein. To accomplish this, a pulmonary artery guide catheter is introduced into the vasculature through a percutaneous incision and guided to the right ventricle using known techniques. For example, the pulmonary artery guide catheter can be inserted into the vasculature via a peripheral vein of the arm (e.g., as with a peripherally inserted central catheter). Changes in a patient's electrocardiography and/or pressure signals from the vasculature can be used to guide and locate the pulmonary artery guide catheter within the patient's heart. Once in the proper location, a guide wire can be introduced into the patient via the pulmonary artery guide catheter, where the guide wire is advanced into the main pulmonary artery and/or one of the pulmonary arteries. Using the guide-wire lumen 926, the catheter 984 can be advanced over the guide wire so as to position the catheter 984 in the main pulmonary artery and/or one or both of the pulmonary arteries of the patient, as described herein. Various imaging modalities can be used in positioning the guide wire of the present disclosure in the main pulmonary artery and/or one of the pulmonary arteries of the patient. Such imaging modalities include, but are not limited to, fluoroscopy, ultrasound, electromagnetic, electropotential modalities.

Using a stimulation system, as discussed herein, stimulation electrical energy can be delivered across combinations of one or more of the electrodes 996. It is possible for the patient's cardiac response to the stimulation electrical energy to be monitored and recorded for comparison to other subsequent tests. It is appreciated that for any of the catheters discussed herein any combination of electrodes, including reference electrodes (as discussed herein) positioned within or on the patient's body, can be used in providing stimulation to and sensing cardiac signals from the patient.

Figure 10:
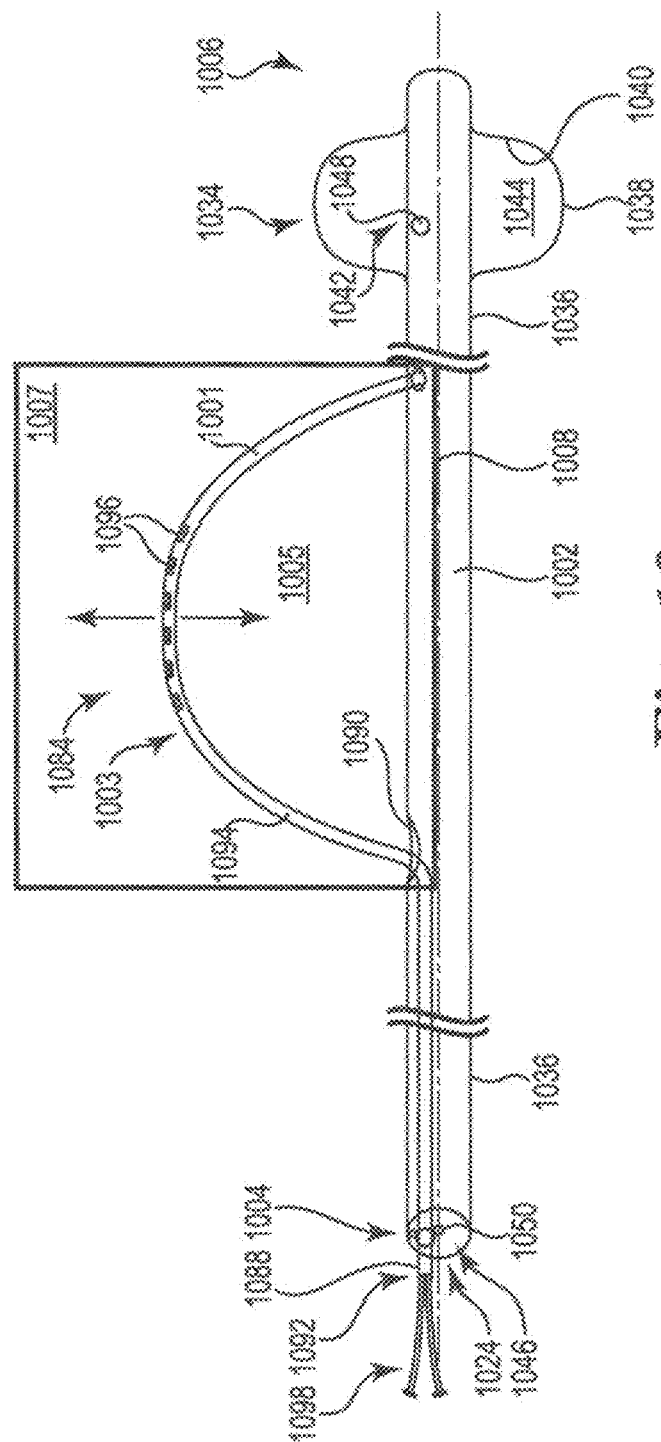
FIG. 10 provides an illustration of an embodiment of the catheter according to the present disclosure.

Referring now to FIG. 10, there is shown an additional embodiment of a catheter 1084 according to the present disclosure. The catheter 1084 can include the features and components as discussed above for catheters 100, 200, 300, 400, 500, 600, 700, 800 and/or 900, a discussion of which is not repeated but the element numbers are included in FIG. 10 with the understanding that the discussion of these elements is implicit. The catheter 1084 illustrates an embodiment in which the elongate electrode member 1094 forms the 1005 loop in a plane 1007 that is perpendicular to the longitudinal center axis of the elongate body.

It is appreciated that more than one of the elongate electrode member can be used with a catheter.

For the various embodiments, the electrode can have a variety of configurations and sizes. For example, the electrodes discussed herein can be ring-electrodes that fully encircle the body on which they are located. The electrodes discussed herein can also be a partial ring, where the electrode only partially encircles the body on which they are located. For example, the electrodes can be partial ring electrodes that preferably only contact the luminal surface of the main pulmonary artery and/or pulmonary arteries, as discussed herein. This configuration may help to localize the stimulation electrical energy, as discussed herein, into the vascular and adjacent tissue structures (e.g., autonomic fibers) and away from the blood. The electrodes and conductive elements provided herein can be formed of a conductive biocompatible metal or metal alloy. Examples of such conductive biocompatible metal or metal alloys include, but are not limited to, titanium, platinum or alloys thereof. Other biocompatible metal or metal alloys are known.

For the various embodiments, the elongate body of the catheters provided herein can be formed of a flexible polymeric material. Examples of such flexible polymeric material include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene); and polyimides, among others.

Each of the catheters discussed herein can further include one or more reference electrodes positioned proximal to the one or more electrodes present on the elongate body. These one or more reference electrodes each include insulated conductive leads that extend from the catheter so as to allow the one or more reference electrodes to be used as common or return electrodes for electrical current that is delivered through one or more of the one or more electrodes on the elongate body of the catheter.

The catheters of the present disclosure can be used to treat a patient with various cardiac conditions. Such cardiac conditions include, but are not limited to, acute heart failure, among others. As discussed herein, the one or more electrodes present on the catheter can be positioned within the main pulmonary artery and/or one or both of the pulmonary arteries. Preferably, the one or more electrodes are positioned in contact the luminal surface of the main pulmonary artery (e.g., in physical contact with the surface of the posterior portion of the main pulmonary artery). As will be discussed herein, the one or more electrodes on the catheter provided herein can be used to provide pulse of electrical energy between the electrodes and/or the reference electrodes. The electrodes of the present disclosure can be used in any one of a unipolar, bi-polar and/or a multi-polar configuration. Once positioned, the catheter of the present disclosure can provide the stimulation electrical energy to stimulate the nerve fibers (e.g., autonomic nerve fibers) surrounding the main pulmonary artery and/or one or both of the pulmonary arteries in an effort to provide adjuvant cardiac therapy to the patient (e.g., electrical cardiac neuromodulation).

In addition to the catheters of the present disclosure, one or more sensing electrodes can be located on or within the patent. Among other things, the sensing electrodes can be used to detect signals indicting changes in various cardiac parameters, where these changes can be the result of the pulse of stimulation electrical energy delivered to stimulate the nerve fibers (e.g., autonomic nerve fibers) surrounding the main pulmonary artery and/or one or both of the pulmonary arteries. Such parameters include, but are not limited to, the patient's heart rate (e.g., pulse), among other parameters. The sensing electrodes can also provide signals indicting changes in one or more electrical parameter of vasculature (electrical activity of the cardiac cycle). Such signals can be collected and displayed, as are known, using known devices (e.g., electrocardiography (ECG) monitor) or a stimulation system, as discussed herein, which receives the detected signals and provides information about the patient.

Other sensors can also be used with the patient to detect and measure a variety of other signals indicting changes in various cardiac parameters. Such parameters can include, but are not limited to, blood pressure, blood oxygen level and/or gas composition of the patient's exhaled breath. For example, catheter of the present disclosure can further include a pressure sensor positioned within or in-line with the inflation lumen for the inflatable balloon. Signals from the pressure sensor can be used to both detect and measure the blood pressure of the patient. Alternatively, the catheter of the present disclosure can include an integrated circuit for sensing and measuring blood pressure and/or a blood oxygen level. Such an integrated circuit can be implemented using 0.18 µm CMOS technology. The oxygen sensor can be measured with optical or electrochemical techniques as are known. Examples of such oxygen sensors include reflectance or transmissive pulse oximetry those that use changes in absorbance in measured wavelengths optical sensor to help determined a blood oxygen level. For these various embodiments, the elongate body of the catheter can include the sensor (e.g., a blood oxygen sensor and/or a pressure sensor) and a conductive element, or elements, extending through each of the elongate body, where the conductive element conducts electrical signals from the blood oxygen sensor and/or the pressure sensor.

The detected signals can also be used by the stimulation system to provide stimulation electrical energy in response to the detected signals. For example, one or more of these signals can be used by the stimulation system to deliver the stimulation electrical energy to the one or more electrodes of the catheter. So, for example, detected signals from the patent's cardiac cycle (e.g., ECG waves, wave segments, wave intervals or complexes of the ECG waves) can be sensed using the sensing electrodes and/or timing parameter of the subject's blood pressure. The stimulation system can receive these detected signals and based on the features of the signal(s) generate and deliver the stimulation electrical energy to the one or more electrode of the catheter. As discussed herein, the stimulation electrical energy is of sufficient current and potential along with a sufficient duration to stimulate one or more of the nerve fibers surrounding the main pulmonary artery and/or one or both of the pulmonary arteries so as to provide neuromodulation to the patient.

Figure 11:
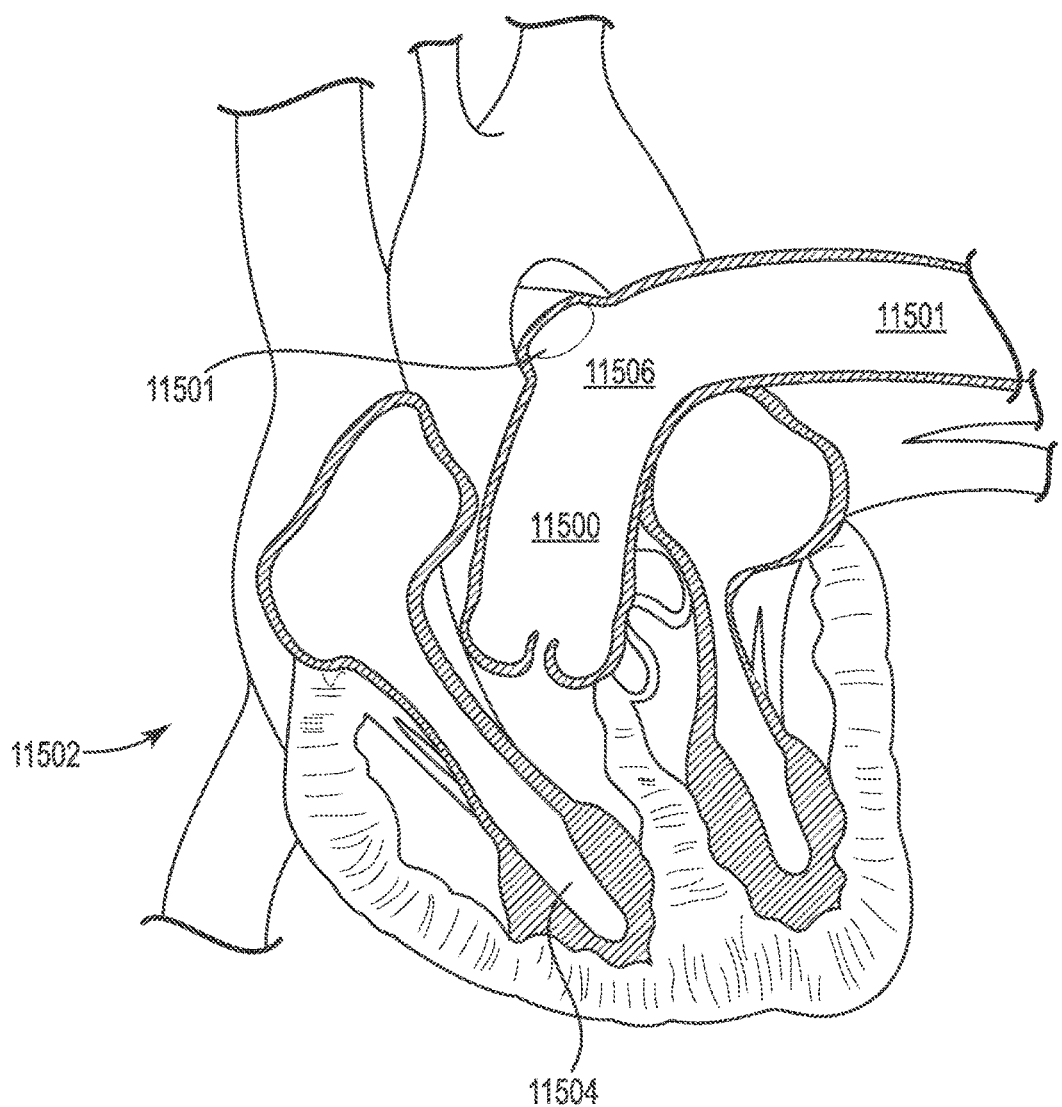
FIG. 11 provides an illustration of a main pulmonary artery of a heart.

Referring now to FIG. 11, there is shown an illustration of a main pulmonary artery 11500 of a heart 11502. The main pulmonary artery 11500 begins at the base of the right ventricle 11504, having a diameter of approximately 3 centimeter (1.2 in) and a length of about approximately 5 centimeters (2.0 in). The main pulmonary artery 11500 branches into two pulmonary arteries (left and right) 11501, which deliver deoxygenated blood to the corresponding lung. As illustrated, the main pulmonary artery 11500 has a posterior surface 11506 that arches over the left atrium and is adjacent the pulmonary vein. As discussed herein, the one or more electrodes of the catheter of the present disclosure are positioned at least partially within the main pulmonary artery and/or a pulmonary artery with the electrode in contact with the posterior surface 11506. One preferred location for positioning the one or more electrodes of the catheter of the present disclosure is the right pulmonary artery as disclosed in U.S. Provisional Patent Application 62/047,313 entitled "METHODS FOR ELECTRICAL NEUROMODULATION OF THE HEART" filed on Sep. 8, 2014, which is incorporated herein by reference in its entirety. Other locations along the lumen of the main pulmonary artery and/or pulmonary arteries are also possible.

Preferably, the one or more electrodes of the catheter of the present disclosure are in contact with the posterior surface 11506 of the main pulmonary artery 11500 and/or pulmonary arteries 11501. From this location, the stimulation electrical energy delivered through the one or more electrodes may be better able to treat and/or provide therapy (including adjuvant therapy) to the patient experiencing a variety of cardiovascular medical conditions, such as acute heart failure. The stimulation electrical energy can elicit responses from the autonomic nervous system that may help to modulate a patient's cardiac contractility. The stimulation electrical energy is intended to affect heart contractility more than the heart rate, thereby helping to improving hemodynamic control while possibly minimizing unwanted systemic effects.

As discussed herein, the catheter of the present disclosure can be positioned in the pulmonary artery of the patient, where the one or more electrodes are positioned in contact the luminal surface of the main pulmonary artery (e.g., in physical contact with the surface of the posterior portion of the main pulmonary artery). The stimulation system is electrically coupled to the one or more electrodes via the conductive elements, where the stimulation system can be used to deliver the stimulation electrical energy to the autonomic cardiopulmonary fibers surrounding the main pulmonary artery.

The stimulation system is used to operate and supply the stimulation electrical energy to the one or more electrodes of the catheter. The stimulation system controls the various parameters of the stimulation electrical energy delivered across the one or more electrodes. Such parameters include control of each electrodes polarity (e.g., used as a cathode or an anode), pulsing mode (e.g., unipolar, bi-polar and/or multi-polar), a pulse width, an amplitude, a frequency, a voltage, a current, a duration, a wavelength and/or a waveform associated with the stimulation electrical energy. The stimulation system may operate and supply the stimulation electrical energy to different combinations and numbers of the one or more electrodes, including the reference electrodes discussed herein. The stimulation system can be external to the patient's body for use by the professional to program the stimulation system and to monitor its performance. Alternatively, the stimulation system could be internal to the patient's body. When located within the patient, the housing of the stimulation system can be used as a reference electrode for both sensing and unipolar pulsing mode.

As discussed herein, the stimulation system can be used to help identify a preferred location for the position of the one or more electrodes along the luminal surface of the main pulmonary artery. To this end, the one or more electrodes of the catheter are introduced into the patient and tests of various locations along the luminal surface of the main pulmonary artery using the stimulation system are conducted so as to identify a preferred location for the electrodes, as discussed herein. During such a test, the stimulation system can be used to initiate and adjust the parameters of the stimulation electrical energy. Such parameters include, but are not limited to, terminating, increasing, decreasing, or changing the rate or pattern of the stimulation electrical energy. The stimulation system can also deliver stimulation electrical energy that are episodic, continuous, phasic, in clusters, intermittent, upon demand by the patient or medical personnel, or preprogrammed to respond to a signal, or portion of a signal, sensed from the patient.

By way of example, the stimulation electrical energy can have a voltage of about 0.1 microvolts to about 75 volts (V), where voltage values of 1 V to 50 V, or 0.1 V to 10 V are also possible. The stimulation electrical energy can be delivered at a frequency of about 1 Hertz (Hz) to about 100,000 Hz, where frequency values of about 2 Hz to about 200 Hz are also possible. The stimulation electrical energy can have a pulse width of about 100 microseconds to about 100 milliseconds. The stimulation electrical energy can also have a variety of wave forms, such as for example, square wave, biphasic square wave, sine wave, or other electrically safe and feasible combinations. The stimulation electrical energy may be applied to multiple target sites simultaneously or sequentially.

An open-loop or closed-loop feedback mechanism may be used in conjunction with the present disclosure. For the open-loop feedback mechanism, a professional can monitor cardiac parameters and changes to the cardiac parameters of the patient. Based on the cardiac parameters the professional can adjust the parameters of the stimulation electrical energy applied to autonomic cardiopulmonary fibers. Non-limiting examples of cardiac parameters monitored include arterial blood pressure, central venous pressure, capillary pressure, systolic pressure variation, arterial blood gases, cardiac output, systemic vascular resistance, pulmonary artery wedge pressure, gas composition of the patient's exhaled breath and/or mixed venous oxygen saturation. Cardiac parameters can be monitored by an electrocardiogram, invasive hemodynamics, an echocardiogram, or blood pressure measurement or other devices known in the art to measure cardiac function. Other parameters such as body temperature and respiratory rate can also be monitored and processed as part of the feedback mechanism.

In a closed-loop feedback mechanism, the cardiac parameters of the patient are received and processed by the stimulation system, as discussed herein, where the parameters of the stimulation electrical energy are adjusted based at least in part on the cardiac parameters. As discussed herein, a sensor is used to detect a cardiac parameter and generate a sensor signal. The sensor signal is processed by a sensor signal processor, which provides a control signal to a signal generator. The signal generator, in turn, can generate a response to the control signal by activating or adjusting one or more of the parameters of the stimulation electrical energy applied by the catheter to the patient. The control signal can initiate, terminate, increase, decrease or change the parameters of the stimulation electrical energy. It is possible for the one or more electrodes of the catheter to be used as a sensor a recording electrode. When necessary these sensing or recording electrodes may delivery stimulation therapy as discussed herein.

The stimulation system can also monitor to determine if the one or more electrodes have dislodged from their position within the main pulmonary artery and/or one or both of the pulmonary arteries (the right pulmonary artery and the left pulmonary artery). For example, the stimulation system can monitor the voltage levels of the stimulation electrical energy delivered and received by the one or more electrodes once the catheter is implanted. If the voltage levels received by the one or more electrode change by a predetermined percentage, a warning signal is produced by the stimulation system and the stimulation electrical energy is stopped.

Figure 12:
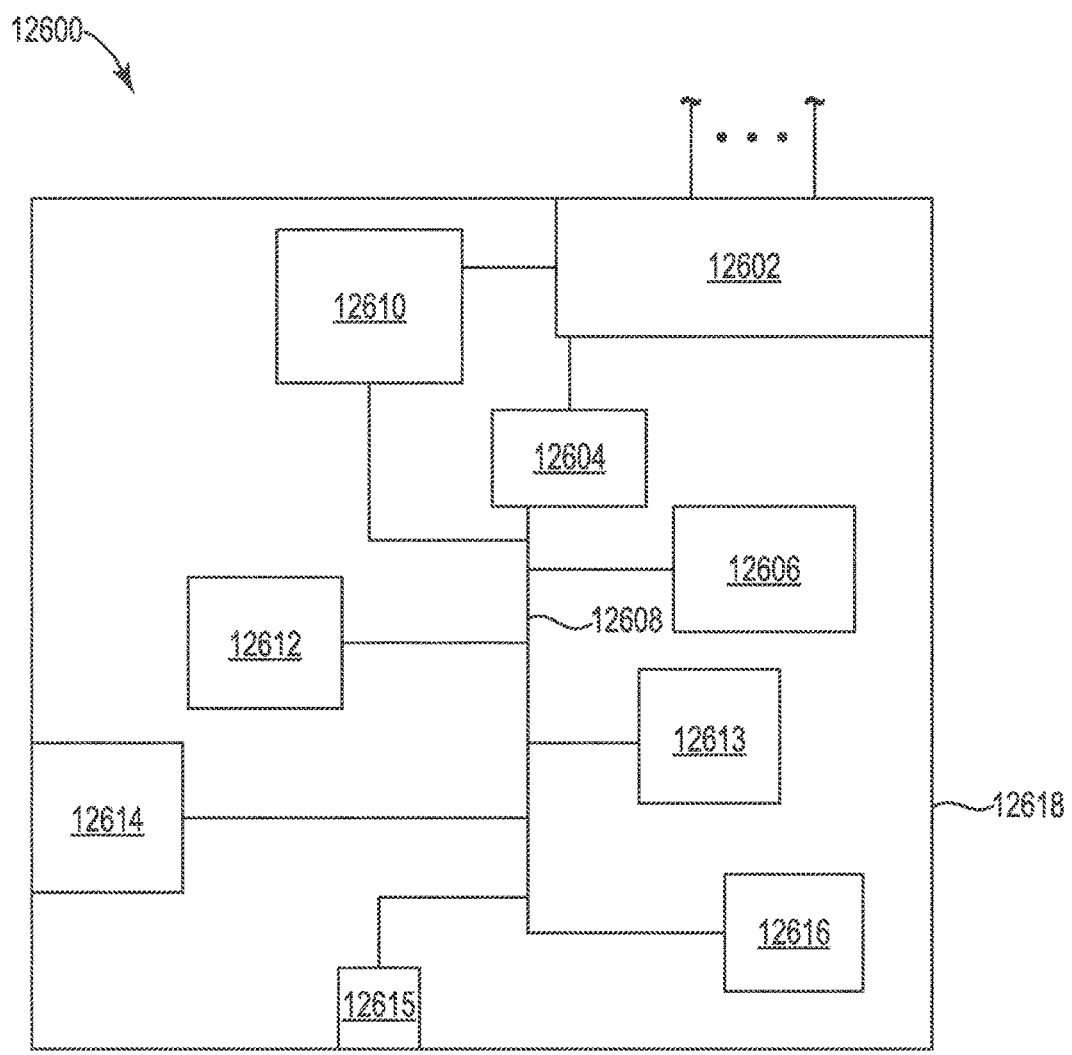
FIG. 12 provides an illustration of a stimulation system for use with the catheter of the present system.

Referring now to FIG. 12, there is shown an embodiment of the stimulation system 12600. The stimulation system 12600 includes an input/output connector 12602 that releasably joins the conductive elements of the catheter of the present disclosure. It is also possible that the conductive elements are permanently coupled to the stimulation system (e.g., not releasably coupled). An input from the sensor can also be releasably coupled to the input/output connector 12602 so as to receive the sensor signal(s) discussed herein.

The input/output connector 12602 is connected to an analog to digital converter 12604. The output of the analog to digital converter 12604 is connected to a microprocessor 12606 through a peripheral bus 12608 including address, data and control lines. Microprocessor 12606 can process the sensor data, when present, in different ways depending on the type of sensor in use. The microprocessor 12606 can also control, as discussed herein, the pulse control output generator 12610 that delivers the stimulation electrical energy to the one or more electrodes via the input/output connector 12602.

The parameters of the stimulation electrical energy can be controlled and adjusted, as needed, by instructions programmed in a memory 12612 and executed by a programmable pulse generator 12613. The instructions in memory 12612 for the programmable pulse generator 12613 can be set and/or modified based on input from the closed-looped system, via the microprocessor 12606. The instructions in memory 12612 for the programmable pulse generator 12613 can also be set and/or modified through inputs from a professional via an input 12614 connected through the peripheral bus 12608. Examples of such an input include a keyboard with a display screen or through a touch screen (not shown), as are known. The stimulation system 12600 can also include a communications port 12615 that connects to the peripheral bus 12608, where data and/or programming instructions can be received by the microprocessor 12606 and/or the memory 12612.

Input from either a professional via the input 12614, the communications port 12615 or from the closed-looped system via the microprocessor 12606 can be used to change (e.g., adjust) the parameters of the stimulation electrical energy. The stimulation system 12600 can also include a power source 12616. The power source 12616 can be a battery or a power source supplied from an external power supply (e.g., an AC/DC power converter coupled to an AC source). The programmable pulse generator 12612 can also include a housing 12618.

The microprocessor 12606 can execute one or more algorithms in order to provide stimulation with closed loop feedback control. The microprocessor 12606 can also be controlled by a professional via the input 12614 to initiate, terminate and/or change (e.g., adjust) the parameters of the stimulation electrical energy. The closed loop feedback control can be used to help maintain one or more of a patient's cardiac parameters at or within a threshold value or range programmed into memory 12612. For example, under closed loop feedback control measured cardiac parameter value(s) can be compared and then it can be determine whether or not the measured value(s) lies outside a threshold value or a pre-determined range of values. If the measured cardiac parameter value(s) do not fall outside of the threshold value or the pre-determined range of values, the closed loop feedback control continues to monitor the cardiac parameter value(s) and repeats the comparison on a regular interval. If, however, the cardiac parameter value(s) from a sensor indicate that one or more cardiac parameters are outside of the threshold value or the pre-determined range of values one or more of the parameters of the stimulation electrical energy will be adjusted by the microprocessor 12606. The adjustments can be made using process control logic (e.g., fuzzy logic, negative feedback, etc.) so as to maintain control of the pulse control output generator 12610.

Although preferred illustrative variations of the present disclosure are described above, it will be apparent to those skilled in the art that various changes and modifications may be made thereto without departing from the embodiments of the present disclosure. It is intended in the appended claims to cover all such changes and modifications that fall within the true spirit and scope of the disclosure.

What is claimed is:

1. A catheter for use in electrical neuromodulation, the catheter comprising:
    an elongate body having a proximal end and a distal end;
    a first opening in the elongate body;
    a second opening in the elongate body, the second opening between the proximal end of the elongate body and the distal end of the elongate body and on a first side of the elongate body;
    a deflection lumen extending between the first opening and the second opening;
    an elongate deflection member having a first end and a second end,
        the deflection lumen having a size configured to allow the deflection member to pass through the deflection lumen,
        the elongate deflection member configured to extend out of the second opening with the first end of the elongate deflection member proximal to the proximal end of the elongate body upon application of pressure to the first end of the elongate deflection member towards the first opening,
        the elongate deflection member comprising a support wire comprising an austenitic metal alloy,
        the support wire configured to provide column strength and a predefined shape to the elongate deflection member upon laterally extending out of the second opening; and
    a plurality of electrodes on a second side of the elongate body, the second side opposite the first side, wherein extension of the elongate deflection member out of the second opening is laterally away from the plurality of electrodes and is configured to bring the plurality of electrodes into contact with a luminal surface of a pulmonary artery.

2. The catheter of claim 1, wherein the support wire comprises a coil shape extending longitudinally along a length of the elongate body, the coil shape configured to transfer longitudinal force applied to the first end of the elongate deflection member through the elongate body so as to laterally extend the second end of the elongate deflection member out of the second opening.

3. The catheter of claim 1, wherein the elongate deflection member comprises a flexible polymeric material, and wherein the support wire is encased in the flexible polymeric material.

4. The catheter of claim 3, wherein the flexible polymeric material comprises medical grade polyurethane, polyester-based polyurethane, polyether-based polyurethane, polycarbonate-based polyurethane, polyamide, polyamide block copolymer, polyolefin, polyethylene, high density polyethylene, or polyamide.

5. The catheter of claim 1, wherein the elongate body comprises a guidewire lumen, wherein the support wire comprises austenitic 316 stainless steel or nickel titanium alloy, and wherein the support wire is encased in a flexible polymeric material.

6. A catheter for use in electrical neuromodulation, the catheter comprising:
    an elongate body having a proximal end and a distal end;
    a first opening in the elongate body;
    a second opening in the elongate body, the second opening between the proximal end of the elongate body and the distal end of the elongate body and on a first side of the elongate body;
    a deflection lumen extending between the first opening and the second opening;
    an elongate deflection member having a first end and a second end, the elongate deflection member configured to extend out of the second opening upon application of pressure to the first end of the elongate deflection member; and
    a plurality of electrodes on a second side of the elongate body, the second side opposite the first side, wherein extension of the elongate deflection member out of the second opening is laterally away from the plurality of electrodes and is configured to bring the plurality of electrodes into contact with a luminal surface.

7. The catheter of claim 6, wherein the elongate deflection member comprises a support wire configured to provide column strength to the elongate deflection member.

8. The catheter of claim 6, wherein the elongate deflection member comprises a support wire comprising austenitic 316 stainless steel or nickel titanium alloy.

9. The catheter of claim 6, wherein the elongate deflection member comprises a support wire configured to provide a predefined shape to the elongate deflection member upon laterally extending out of the second opening.

10. The catheter of claim 6, wherein the elongate deflection member comprises a support wire comprising a coil shape extending longitudinally along a length of the elongate body, and wherein the coil shape is configured to transfer longitudinal force applied to the first end of the elongate deflection member through the elongate body so as to laterally extend the second end of the elongate deflection member out of the second opening.

11. The catheter of claim 6, wherein the elongate deflection member comprises a flexible polymeric material.

12. The catheter of claim 11, wherein the elongate body comprises a guidewire lumen, wherein the elongate deflection member comprises a support wire and a flexible polymeric material, wherein the support wire comprises austenitic 316 stainless steel or nickel titanium alloy, and wherein the support wire is encased in the flexible polymeric material.

13. A catheter for use in electrical neuromodulation, the catheter comprising:
- an elongate body having a proximal end and a distal end;
- a first opening in the elongate body;
- a second opening in the elongate body, the second opening between the proximal end of the elongate body and the distal end of the elongate body;
- a deflection lumen extending between the first opening and the second opening;
- an elongate deflection member having a first end and a second end, the elongate deflection member configured to extend out of the second opening; and
- a plurality of electrodes, wherein extension of the elongate deflection member out of the second opening is laterally away from the plurality of electrodes and is configured to bring the plurality of electrodes into contact with a luminal surface.

14. The catheter of claim 13, wherein the elongate deflection member comprises a support wire configured to provide column strength to the elongate deflection member.

15. The catheter of claim 13, wherein the elongate deflection member comprises a support wire comprising austenitic 316 stainless steel or nickel titanium alloy.

16. The catheter of claim 13, wherein the elongate deflection member comprises a support wire configured to provide a predefined shape to the elongate deflection member upon laterally extending out of the second opening.

17. The catheter of claim 13, wherein the elongate deflection member comprises a support wire comprising a shape configured to transfer longitudinal force applied to the first end of the elongate deflection member through the elongate body so as to laterally extend the second end of the elongate deflection member out of the second opening.

18. The catheter of claim 17, wherein the shape comprises a coil shape.

19. The catheter of claim 13, wherein the elongate deflection member comprises a flexible polymeric material.

20. The catheter of claim 13, wherein the elongate body comprises a guidewire lumen, wherein the elongate deflection member comprises a support wire and a flexible polymeric material, wherein the support wire comprises austenitic 316 stainless steel or nickel titanium alloy, and wherein the support wire is encased in the flexible polymeric material.

* * * * *